(12) United States Patent
Subramaniam et al.

(10) Patent No.: US 11,249,068 B2
(45) Date of Patent: Feb. 15, 2022

(54) NON-INVASIVE METHOD FOR DETECTING A DEADLY FORM OF MALARIA

(71) Applicant: Ohio State Innovation Foundation, Columbus, OH (US)

(72) Inventors: Vishwanath V. Subramaniam, Westerville, OH (US); Mark Drew, Columbus, OH (US); Brad Smith, Celina, OH (US); Joseph West, Richwood, OH (US); Travis H. Jones, West Chester, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 0 days.

(21) Appl. No.: 15/774,657

(22) PCT Filed: Nov. 9, 2016

(86) PCT No.: PCT/US2016/061019
§ 371 (c)(1),
(2) Date: May 9, 2018

(87) PCT Pub. No.: WO2017/083317
PCT Pub. Date: May 18, 2017

(65) Prior Publication Data
US 2019/0257815 A1    Aug. 22, 2019

Related U.S. Application Data

(60) Provisional application No. 62/252,779, filed on Nov. 9, 2015.

(51) Int. Cl.
*G01N 33/49* (2006.01)
*A61B 5/053* (2021.01)
(Continued)

(52) U.S. Cl.
CPC ............. *G01N 33/49* (2013.01); *A61B 5/053* (2013.01); *A61B 5/14546* (2013.01); *C12Q 1/04* (2013.01);
(Continued)

(58) Field of Classification Search
CPC combination set(s) only.
See application file for complete search history.

(56) References Cited

U.S. PATENT DOCUMENTS

| 4,250,451 A | 2/1981 | Slagle |
| 4,646,754 A | 3/1987 | Seale |

(Continued)

FOREIGN PATENT DOCUMENTS

| WO | 2002076294 A2 | 10/2002 |
| WO | 2005057467 A2 | 6/2005 |

OTHER PUBLICATIONS

Peng, Weng Kung, et al. "Micromagnetic resonance relaxometry for rapid label-free malaria diagnosis." Nature medicine 20.9 (2014): 1069.*

(Continued)

*Primary Examiner* — Robert J Eom
(74) *Attorney, Agent, or Firm* — Standley Law Group LLP

(57) ABSTRACT

A non-invasive, continuous, and direct system for detecting the presence of malaria parasites that exploits the paramagnetic properties of hemozoin in red blood cells. An electromagnetic probe (EM probe) is comprised of a dual coaxial coil used to detect iron oxide particles by using sensitive lock-in amplification of detector voltage or phase shift.

25 Claims, 17 Drawing Sheets

(51) Int. Cl.
*A61B 5/145* (2006.01)
*C12Q 1/04* (2006.01)

(52) U.S. Cl.
CPC ........ *G01N 2333/445* (2013.01); *Y02A 50/30* (2018.01)

(56) References Cited

U.S. PATENT DOCUMENTS

| | | |
|---|---|---|
| 4,690,149 A | 9/1987 | Ko |
| 4,947,678 A | 8/1990 | Hori et al. |
| 5,390,673 A | 2/1995 | Kikinis |
| 5,514,337 A | 5/1996 | Groger et al. |
| 5,810,742 A | 9/1998 | Pearlman |
| 6,418,335 B2 | 7/2002 | Avrin et al. |
| 6,485,427 B1 | 11/2002 | Lee et al. |
| 6,813,515 B2 | 11/2004 | Hashimshony |
| 6,876,878 B2 | 4/2005 | Zhdanov |
| 7,283,868 B2 | 10/2007 | Ko et al. |
| 7,505,811 B2 | 3/2009 | Hashimshony |
| 7,865,236 B2 | 1/2011 | Cory et al. |
| 8,214,006 B2 | 7/2012 | Newman et al. |
| 8,438,927 B2 | 5/2013 | Shekhawat et al. |
| 9,844,347 B2 | 12/2017 | Subramaniam et al. |
| 2003/0016010 A1 | 1/2003 | Kandori et al. |
| 2003/0055358 A1 | 3/2003 | Ko et al. |
| 2005/0090732 A1 | 4/2005 | Ivkov et al. |
| 2006/0085049 A1 | 4/2006 | Cory et al. |
| 2006/0293597 A1 | 12/2006 | Johnson et al. |
| 2008/0021343 A1 | 1/2008 | Hashimshony et al. |
| 2008/0204009 A1 | 8/2008 | Gleich et al. |
| 2008/0224688 A1 | 9/2008 | Rubinsky et al. |
| 2008/0234574 A1 | 9/2008 | Hancock et al. |
| 2008/0246472 A1 | 10/2008 | Igney et al. |
| 2010/0033174 A1 | 2/2010 | Gleich et al. |
| 2010/0156414 A1* | 6/2010 | Sakellariou .......... G01R 33/307 324/309 |
| 2011/0034974 A1 | 2/2011 | Marquez et al. |
| 2011/0192731 A1 | 8/2011 | Bhattacharya |
| 2011/0196239 A1* | 8/2011 | Behrend ............... G06T 7/0014 600/476 |

OTHER PUBLICATIONS

Kim, Kiho, J. R. Bodart, and N. S. Sullivan. "High-Sensitivity CW NMR Probe for Low Temperatures and Ultrahigh Frequencies." Journal of Magnetic Resonance, Series A 118.1 (1996): 28-32.*

Webb, Andrew G. "Radiofrequency microcoils in magnetic resonance." Progress in Nuclear Magnetic Resonance Spectroscopy 31.1 (1997): 1-42.*

Smith, Brad. A Non-Invasive Method for Detecting a Deadly Form of Malaria: Plasmodium Falciparum. Diss. The Ohio State University, 2014. (Year: 2014).*

Murray, C. et al., Global Malaria Mortality Between 1980 and 2010: A Systematic Analysis, The Lancet, Feb. 4, 2012, pp. 413-431, vol. 379.

Thompson, M. et al., Plasmodium Falciparum Response to Oscillating Weak Magnetic Fields, Apr. 26, 2011.

Johns Hopkins Bloomberg School of Public Heath, About Malaria, site visited Feb. 1, 2013, <http://www.cdc.gov/malaria/diagnosis_treatement/rdt.html>.

Akompong, T. et al., In Vitro Activity of Riboflavin Against the Human Malaria Parasite Plasmodium Falciparum, Antimicrobial Agents and Chemotherapy, Jan. 2000, pp. 88-96, vol. 44, No. 1.

Centers for Disease Control and Prevention, Malaria Diagnosis (U.S.)—Rapid Diagnostic Test, site visited Feb. 8, 2010, <http://www.cdc.gov/malaria/diagnosis_treatment/rdt.html>.

Centers for Disease Control and Prevention, Malaria Diagnosis (U.S.)—Microscopy, site visited Nov. 9, 2012, <http://www.cdc.gov/malaria/diagnosis_treatment/microscopy.html>.

Milne, L. et al., Accuracy of Routine Laboratory Diagnosis of Malaria in the United Kingdom, J. Clin Pathol, 1994, pp. 740-742, vol. 47.

McFerran, J., An Electromagnetic Method for Cancer Detection, The Ohio State University, PhD Dissertation, 2009.

Sequin, E., Imaging of Cancer in Tissues Using an Electromagnetic Probe, The Ohio State University, Master's Thesis, 2009.

Wilson, M., Design and Fabrication of an Electromagnetic Probe for Biomedical Applications, The Ohio State University, Master's Thesis, 2011.

Zimmerman, P. et al., Diagnosis of Malaria by Magnetic Deposition Microscopy, The American Journal of Tropical Medicine and Hygiene., Apr. 2006, pp. 568-572.

Newman, D. et al., A Magneto-Optic Route toward the In Vivo Diagnosis of Malaria: Preliminary Results and Preclinical Trial Data, Biophysical Journal, Jul. 2008, pp. 994-1000, vol. 95.

Ongagna-Yhombi, S. et al., Improved Assay to Detect Plasmodium Falciparum Using an Uninterrupted, Semi-Nested PCR and Quantitative Lateral Flow Analysis, Malaria Journal, 2013, pp. 1-8.

Stucker, M. et al., Capillary Blood Cell Velocity in Human Skin Capillaries Located Perpendicularly to the Skin Surface: Measured by a New Laser Doppler Anemometer, Microvascular Research 52, 1996, pp. 188-192.

Antonios, T. et al., Structural Skin Capillary Rarefraction in Essential Hypertension, Hypertension 33.4, 1999, pp. 998-1001.

Kapishnikov, S. et al., Oriented Nucleation of Hemozoin at the Digestive Vacuole Membrane in Plasmodium Falciparum, Proceedings of the National Academy of Sciences, Jul. 10, 2012, p. 11188-11193, vol. 109, No. 28.

Gencer et al., Imaging Tissue Conductivity via Contactless Measurements: A Feasibility Study. Elektrik, vol. 6, No. 3, 1998.

Korjenevsky et al., Magnetic induction tomography: experimental realization, 2000, IOP Publishing Ltd.

Richer et al., Eddy Current Based Flexible Sensor for Contactless Measurement of Breathing, Instrumentation and Measurement Technology Conference, Ottawa, Canada, May 17-19, 2005.

Ambia et al., Electrical Impedance Imaging Using Eddy Current, Proceedings of World Academy of Science, Engineering and Technology, vol. 30, Jul. 30, 2008.

Wansapura et al., Temperature Mapping of Frozen Tissue Using Eddy Current Compensated Half Excitation RF Pulses, Magnetic Resonance in Medicine, pp. 985-992, 2001.

Sharma, et al., Transmission of Time Varying Magnetic Field Through Body Tissue, Journal Biological Physics, vol. 3, pp. 95-102, 1975.

* cited by examiner

NON-INVASIVE METHOD FOR DETECTING A DEADLY FORM OF MALARIA

CROSS-REFERENCE TO RELATED APPLICATIONS

This application claims priority to provisional U.S. Application No. 62/252,779 filed on Nov. 9, 2015 and is herein incorporated by reference in its entirety.

BACKGROUND OF THE INVENTIVE FIELD

The present invention is directed to non-invasive method for detecting a deadly form of malaria—*Plasmodium falciparum*. Malaria is an infectious disease transmitted by mosquitoes that affects 40% of the world's population, resulting in 300 to 500 million new infections yearly. Due to severe poverty, the most effective combative measures (bed nets, spray DDT and draining standing water) against mosquitoes that carry the deadly parasite are often not widely accessible in these countries.

Of the different species of malaria, *Plasmodium falciparum* (PF) is the most prevalent and deadly in humans. While treatment is available, PF is often difficult to detect with a blood draw because the parasite sequesters in internal organs during various phases of its reproductive cycle. PF infects red blood cells, converting the hemoglobin in the red blood cells into iron rich particles called hemozoin. The hemozoin crystals can be as large as 1 μm in size and several clusters are stored in the food vacuoles of the parasite. PF is predominant in low and middle-income countries where pathologists and microscopes are not widely available to confirm the presence of this species of malaria.

Consequently, an inexpensive, non-invasive, continuous, and direct indicator of PF is needed. The present invention exploits the paramagnetic properties of hemozoin and relates to a non-invasive, electromagnetic method of detecting infected red blood cells.

SUMMARY OF THE GENERAL INVENTIVE CONCEPT

In one embodiment of the invention, an electromagnetic probe (EM probe) is comprised of a dual coaxial coil used to detect iron oxide particles by using sensitive lock-in amplification of detector voltage. The probe is used to detect iron oxide particles (e.g., less than 44 μm-720 μm).

Results show that measurements of micron sized iron particles on the scale of less than 44 microns are repeatable. Preliminary measurements with food vacuoles trapped in small capillary tubes confirm feasibility of the method with indicated voltage differences of 44.7±25.7 mV versus voltage readings for a control (capillary tube without trapped food vacuoles) of 16.2 1±4.3 mV with great potential for increased sensitivity. The present invention provides an alternative to existing methods (mainly peripheral blood draws) for the detection of PF.

In addition to being noninvasive, the method described herein can provide detection results that can be interpreted in simple binary fashion (e.g. a readout red LED lighting up indicating the presence of infected cells and a green LED lighting up indicating no infection). This method therefore potentially lends itself to infected individuals being able to monitor themselves continuously throughout the day and getting timely treatment after confirmation, without the need for a peripheral blood draw, or the presence of a trained pathologist to interpret the microscopic examination of the drawn blood.

In one embodiment of the invention, the invention is comprised of: a probe, in electrical communication with a current or power supply, shaped in a configuration so that it may be hand-held comprising a coaxially wound dual coil that contains a primary coil (driver) and a detector coil; a measurement system, operably connected to the probe and configured to measure a phase shift or amplitude change in the voltage or current produced thereby in the detector coil when the primary and detector coils are positioned adjacent to the blood; a capacitance electrically connected to the detector coil for enhancing sensitivity of the probe; a ballast resistance in electrical communication with the primary coil to enable the current on the primary coil to follow the applied voltage; a processing system operably connected to the measurement system, the processing system programmed with one or more software routines executing on the processing system to: 1) detect the presence of malaria parasites based upon the phase shift or amplitude change measured by the measurement system, and 2) generate a signal used to provide an alert when malaria is detected; and wherein the voltage or current produced in the detector coil has at least a first and second duty cycle each comprised of multiple peaks and wherein the primary coil and detector coil has inductances and capacitances so the last peak of the voltage or current produced in the first duty cycle coincides on a sloping side of the first peak of the second duty cycle. In another embodiment of the invention, the driver and primary coils are adjacent to each other.

The foregoing and other features and advantages of the present invention will be apparent from the following more detailed description of the particular embodiments, as illustrated in the accompanying drawings.

BRIEF DESCRIPTION OF THE DRAWINGS

In addition to the features mentioned above, other aspects of the present invention will be readily apparent from the following descriptions of the drawings and exemplary embodiments, wherein like reference numerals across the several views refer to identical or equivalent features, and wherein.

DETAILED DESCRIPTION OF EXEMPLARY EMBODIMENT(S)

The following detailed description of the example embodiments refers to the accompanying figures that form a part thereof. The detailed description provides explanations by way of exemplary embodiments. It is to be understood that other embodiments may be used having mechanical and electrical changes that incorporate the scope of the present invention without departing from the spirit of the invention.

Figure 1:
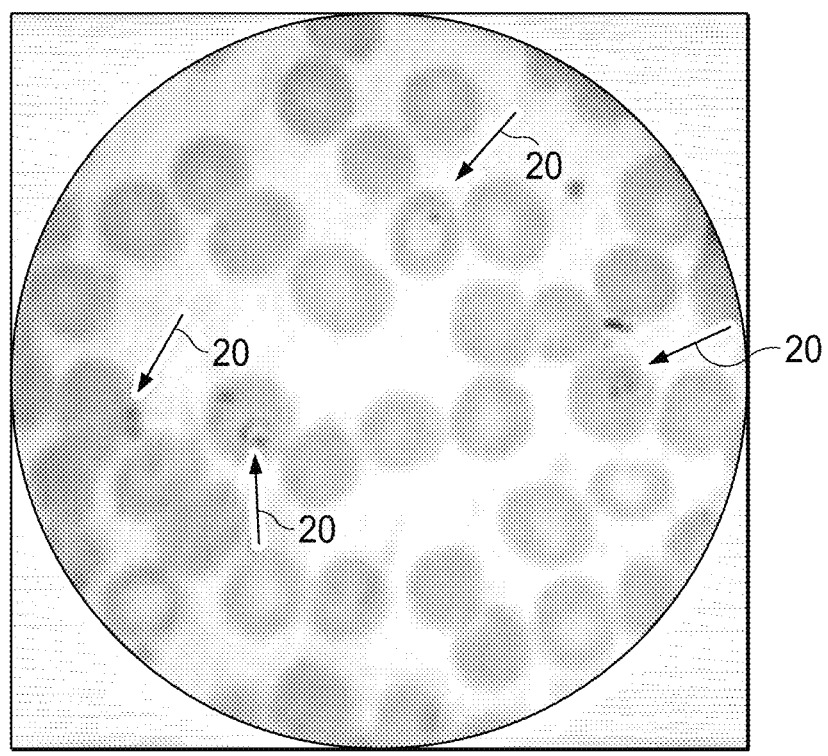
FIG. 1 shows a typical microscopic image of cells obtained from a blood sample infected with PF parasites.

There are currently two main ways to detect for malaria, and in particular *Plasmodium falciparum* (PF). These are a peripheral blood draw followed by analysis of red blood cells using an optical microscope, and the Rapid Diagnostic Test (RDT). An RDT is a quicker way to detect if certain types of malaria are present in the blood stream by placing a blood sample on a test card. After about 15 minutes, line indicators notify the user if any forms of malaria exist in the bloodstream. While this process is quick, it also necessitates an invasive blood draw and does not eliminate the need for analysis using a microscope when the results of an RDT are negative or inconclusive. The state of the art in detecting PF is microscopy, which requires a skilled technician or pathologist who must examine a blood sample from the patient under a microscope. FIG. 1 shows a typical microscope image of cells obtained from a blood sample infected with PF parasites. Visible in the figure are the dark specks that are the hemozoin crystals 20 within the food vacuoles of the parasite.

The disadvantages of microscopy are that these results are only as reliable as the individual or lab performing the analysis, and the fact that PF is not always present in the blood stream at the time of the peripheral blood draw. Microscopy is also impractical in rural areas of LMICs plagued by poverty, lack of equipment, lack of skilled labor, and lack of education.

Compounding the problem of detecting PF is that even when pathology facilities are available, sizeable errors in diagnosis do occur. False positive rates can be as high as 36% and false negatives 18% since PF is not always present in the blood stream as it sequesters in capillaries. Therefore, there is a critical need for an inexpensive, accurate, easy to monitor, and non-invasive method of detecting PF.

Electromagnetic Detection

The present invention focuses on detecting paramagnetic particles on the scale of microns using an electromagnetic (EM) probe. An EM probe is comprised of coaxially wound inner and outer coils. The inner coil is used to produce the magnetic field that induces a voltage and current in the outer coil through inductive coupling. A change in the inductive interaction between the two coils occurs when a conductive or magnetic sample is placed inside the concentric coil arrangement causing a modification in the voltage and current characteristics of the outer coil. With the inner coil serving as the primary, the outer coil then acts as the detector.

Using a function generator to produce a voltage on the inner coil and thus driving a time varying current through the inner coil, results in a time varying magnetic field, according to Ampere's Law. This time varying magnetic field around the inner coil causes a current to be induced in the outer detector coil by Faraday's Law. With a time-varying current now in the outer coil, it also creates its own magnetic field that interacts with the inner coil. The sample placed inside these two coaxial, mutually coupled coils will alter this interaction, producing a small change in the voltage in the outer coil that can be detected using lock-in detection.

Research has been conducted on eddy current detection of cancer. EM probes combined with lock-in amplification have shown that there is both a phase and magnitude difference between cancer bearing and normal tissue. The same principals are used in present invention to show that a minute paramagnetic concentration of iron produces a detectable difference in both phase and magnitude. These differences are recognized as an altered detector coil voltage just as they are in the detection of cancer.

The magnetic properties of hemozoin have been described in previous studies. These are magnetic deposition microscopy, magneto-optic spectroscopic detection, and PCR (polymerase chain reaction) methods. Magnetic deposition microscopy has shown that bringing a magnet in proximity to a blood smear of malaria infected blood results in the parasite concentrating at a specific point on the slide where the magnetic field is greatest. This allows for just one area of the slide to be examined for any signs of infection. Detection of malaria in suspensions with the eventual hope of detecting the parasite in vivo has been studied previously using a magneto-optic method. This method has been shown to be accurate when conducted on suspensions using the magnetic properties of hemozoin, but in vivo measurements have not yet been demonstrated. The final method, PCR, uses saliva or dried blood in the detection of PF. This is also a way to detect PF non-invasively, but requires an expensive technology and expertise, and is not a continuous type of detection, as a sample still needs to be acquired before this detection method can be utilized. This research uses a few of the same concepts as some of those from previous work, but uses a new method in electromagnetic detection.

Figure 2:
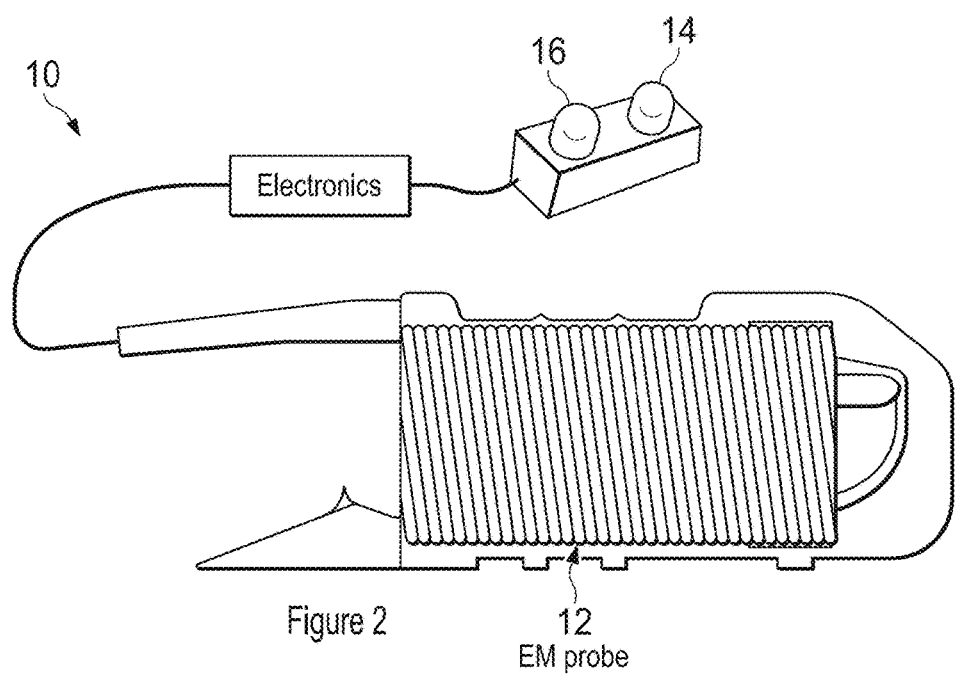
FIG. 2 illustrates one embodiment of a EM probe detection system.

The paramagnetic properties of hemozoin can be utilized to develop an electromagnetic method of detecting infected red blood cells. The advantages of such an approach are that (1) it can be non-intrusive, i.e., blood need not be drawn, (2) its results can be interpreted in a simple binary fashion (e.g. red LED 14 lighting up when infected cells are present and a green LED 16 for no sign of infection), and (3) that a potentially infected individual can monitor themselves multiple times a day or even continuously without the need for a blood draw, and (4) that there is no need for a skilled pathologist to interpret the results. FIG. 2 illustrates one embodiment of a EM probe detection system 10.

The present invention is used to detect the presence of iron oxide particles using an electromagnetic (EM) probe 12 and lock-in detection. It is important to demonstrate that it is possible for the new method to detect iron oxide particles of substantial size before doing so on smaller particles of relevance to PF.

The present invention also optimizes the EM probe for detection of these smaller micron sized iron oxide particles. This is necessary so that the EM probe is not only capable of detecting iron oxide particles, but also capable of detecting particles that are on the same scale as those that will be found in the food vacuoles within the parasite. As previously discussed, the food vacuoles contain the iron rich waste known as hemozoin, which is on the scale of one micron per each food vacuole. When a human host has contracted PF, the scale of hemozoin that must be able to be detected will be larger than one micron due to the percent of PF infected red blood cells (level of parasitemia) in the body during an infection.

The present invention also demonstrates the feasibility of detecting these hemozoin particles in food vacuoles in vitro using the EM probe. This involves taking a pre-sorted sample of isolated food vacuoles from PF infected human blood and placing them inside a capillary tube which can be inserted into the EM probe. This demonstrates that the hemozoin can be detected by the EM probe and is a big step towards detecting PF infected blood in vivo using the EM probe.

Overview of the Design of the EM Probe

The EM probe developed for the present invention is based on the design methodology of an earlier series of probes labeled the A-series, which were used in previous works for detection and imaging of cancer. The A-series of coils are comprised of a primary side with 2 inner layers and an outer detector coil comprising 6 layers. In this embodiment, the coil designed for detecting PF was wound as tightly as possible to the sample capillary tube in order to perform measurements on particles microns in size. It is presumed that the farther the sample is away from the detector coil, the less the signal that would be detectable.

Figure 3:
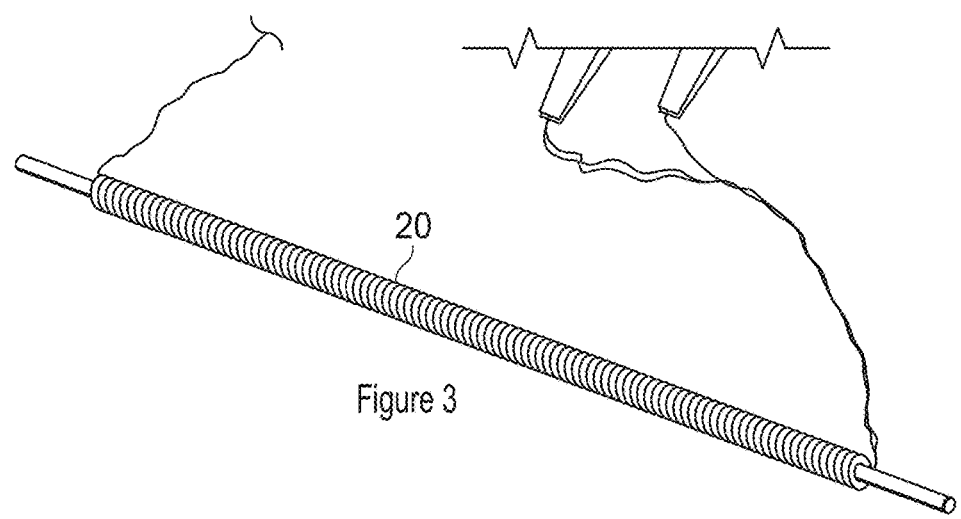
FIG. 3 illustrates the PF1 EM probe.
Figure 4:
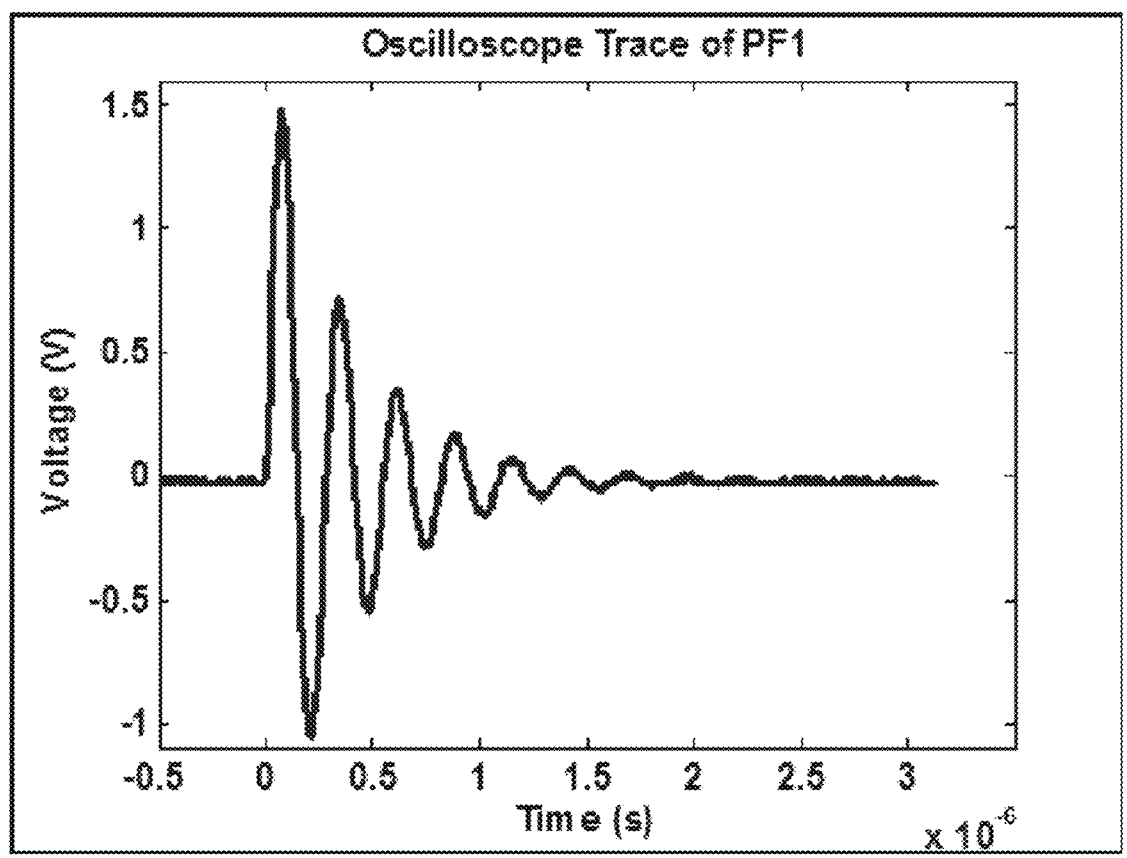
FIG. 4 illustrates typical voltage variation over a single cycle of the primary (inner) coil of PF1.

With these design constraints in mind, PF1 was fabricated. PF1 consists of a concentrically wound dual coil that contains only 1 inner layer and 1 outer layer around a rod of spring steel of a slightly larger in diameter (1.45 mm) than that of the same glass capillary tubes (outer diameter of 1.10 mm) in which samples such as food vacuoles or micron sized iron oxide particles can be placed. This 1 by 1 coil design is a simplification of the earlier coils used in the cancer detection studies. With only 1 inner layer and 1 outer layer, the coil is easier and less expensive to manufacture. The 1 by 1 coil has a much lower self-inductance (2.4 µH for the inner coil and 4.5 µH for the outer coil) compared to the earlier A-series (69.6 µH for the inner coil and 475.5 µH for the outer coil). The coil parameters of PF1 are given in Table 1. FIG. 3 illustrates the PF1 EM probe 20. Resistances and self-inductances were measured using an Extech Instruments LCR Meter (Model 380193). The capacitance of each coil cannot be measured accurately and was therefore inferred in the following manner. Using a previously developed circuit element model, the governing equations are numerically integrated to predict detector and primary coil voltages as a function of time. These predictions are then compared to experimental measurements (e.g. see FIG. 4) made on each coil while varying the capacitance. FIG. 1 illustrates typical voltage variation over a single cycle of the primary (inner) coil of PF1 displayed on an oscilloscope.

TABLE 1

PF1 EM Probe Parameters

| | Characteristic | | | | | |
|---|---|---|---|---|---|---|
| | Coil Diameter (mm) | Length (mm) | # of Turns | Resistance (Ω) | Inductance (µH) | Capacitance* (pF) |
| Inner Coil | 1.45 | 81.30 | 290 | 1.397 | 2.4 | 190 |
| Outer Coil | 3.25 | 81.30 | 290 | 1.661 | 4.5 | 190 |

*Capacitance estimated using derivation equations and matching to experimental oscilloscope trace Initial measurements using PF1 were encouraging. However, certain flaws in its design had to be corrected. In particular, since the diameters of the capillary tubes containing the samples of iron oxide or food vacuoles were so close in dimension to PF1's inner diameter, there was a tendency to rub, resulting in unraveling of some of the windings of the inner coil of PF1. Therefore, a second coil, PF2, was designed and fabricated.

Figure 5:
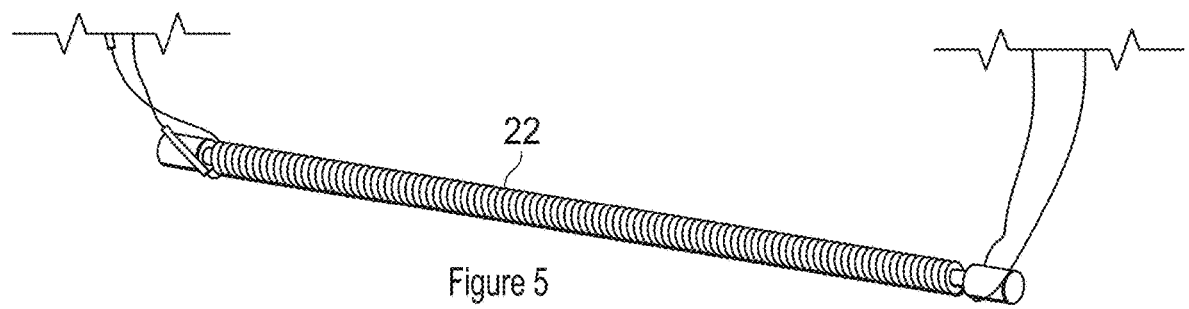
FIG. 5 illustrates the PF2 EM probe.
Figure 6:
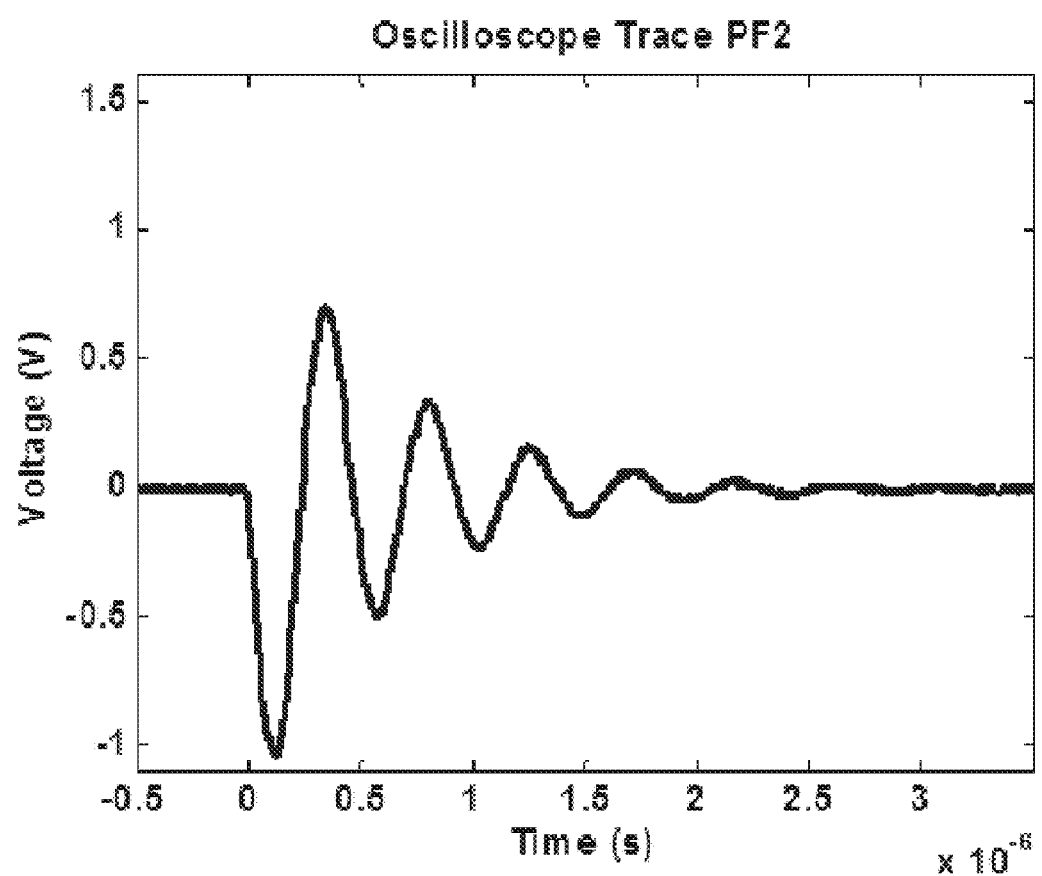
FIG. 6 illustrates typical voltage variation over a single cycle of the primary (inner) coil of PF2 displayed on an oscilloscope.

The second EM probe, PF2, was designed with a solid, non-conductive, hollow cylinder made of PVC, with an inside diameter of 1.45 mm and an outside diameter of 3.30 mm. All other parameters such as inductances and resistances were as close as possible to those of PF1. PF2 is also a 1 by 1 concentrically wound coil with the characteristics listed in Table 2. Resistances and self-inductances of the coils were measured using an Extech Instruments LCR Meter (Model 380193). The capacitances were again found by matching the voltage traces predicted by numerical integration of the governing equations of a circuit element model and comparing them with the corresponding voltage traces measured on an oscilloscope. FIG. 5 illustrates the PF2 EM probe 22. FIG. 6 illustrates typical voltage variation over a single cycle of the primary (inner) coil of PF2 displayed on an oscilloscope.

TABLE 2

PF2 EM Probe Parameters

| | Characteristic | | | | | |
|---|---|---|---|---|---|---|
| | Coil Diameter (mm) | Length (mm) | # of Turns | Resistance (Ω) | Inductance (µH) | Capacitance* (pF) |
| Inner Coil | 3.30 | 81.40 | 315 | 2.107 | 11.7 | 185 |
| Outer Coil | 4.25 | 81.40 | 315 | 2.342 | 15.1 | 185 |

*Capacitance estimated using derivation equations and matching to experimental oscilloscope trace In the discussion of the results of measurements with both prototypes, it will be shown how the sensitivity differs between PF1 and PF2 as a result of differences in their diameters. Details of the fabrication of each probe is discussed next in the following section.

Figure 7:
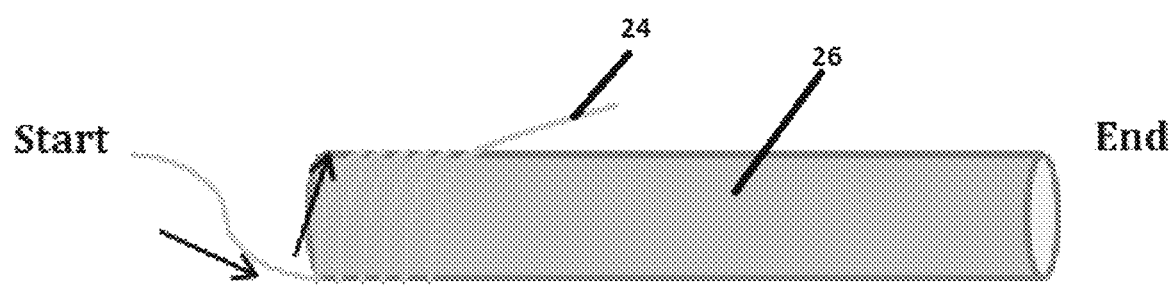
FIG. 7 illustrates the beginning winding of the coil around a core.

FIG. 7 illustrates the beginning winding of the coil 24 around a core 26. The coil is preferably wound counter-clockwise when looking down the core from the start. Each EM probe is fabricated using 32 American Wire Gauge (AWG) insulated copper wire (diameter of 0.202 mm). The inner layer is wrapped tightly by hand around the core used for each wire in a counterclockwise rotation as seen in FIG. 7. For PF1, a mandrel made of spring steel with a diameter of 1.45 mm was used, which was then slid off, leaving an empty air core. PF2 was wrapped around a permanent core of hollow PVC plastic with an inner diameter of 1.45 mm and an outer diameter of 3.30 mm. After the first layer was completed by carefully tightly winding so that there are no air gaps between windings, a layer of Clear Gloss 01, Sally Hansen Hard as Nails Color nail polish was applied to the entire outer layer of the inner coil. After allowing this layer of polish to dry, the outer layer was wound in the same fashion as the inner layer and in the same direction. The outer layer started at the same end as the inner coil start and again was wound by hand in a counterclockwise motion. It is again important to keep the windings as tightly packed as possible. Once the outer layer is complete, another layer of nail polish was applied to the outer layer of the outer coil. All loose ends of the coils were marked with either electrical tape or heat shrink to signify the end of the coil. This is important to note when finding those orientations of the coil that are most sensitive.

A description of the measurement system involving the EM probe is described below. The measurement consists of first using a function generator to drive a transient current through the primary side of the EM probe. The induced current in the detector coil is then monitored as a voltage output to an oscilloscope or to a lock-in amplifier whose output in turn can be viewed on an oscilloscope. As a sample such as an iron oxide specimen or iron-rich food vacuoles is placed inside the EM probe (i.e., inside the inner coil which is the primary coil), the mutual coupling between primary and detector coils is altered registering a change in the voltage recorded by the lock-in amplifier.

Figure 8:
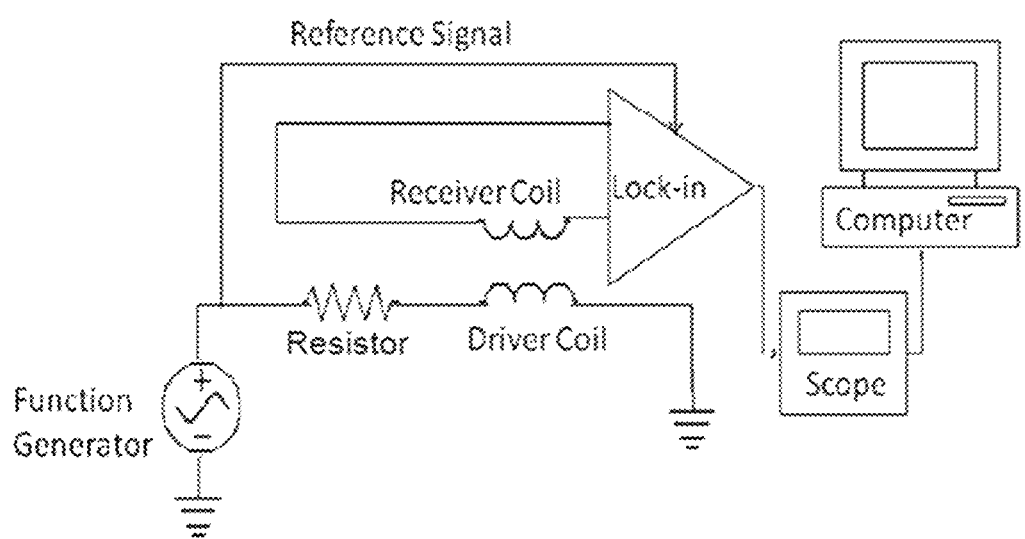
FIG. 8 illustrates one embodiment of the measurement system of the present invention.

FIG. 8 illustrates one embodiment of the measurement system of the present invention. A 99 kHz sawtooth waveform at 7-10 Vpp voltage is imposed on the EM probe through a ballast resistor (800-1020 Ohms) on the primary coil, using a Hewlett Packard 33120A 15 MHz function/arbitrary waveform generator. As shown in FIG. 8, a Stanford Research Systems, SR510 Lock-in Amplifier is used to measure the amplitude and phase of the voltage signal from the detector coil. The lock-in amplifier is used to extract otherwise small signals from noise. This lock-in generator DC signal is then output to a DSOX2014A, 100 MHz, 4 Channel Oscilloscope for data collection. The output on the oscilloscope is then recorded in .csv format to a flash drive to be used for analysis.

Figure 9:
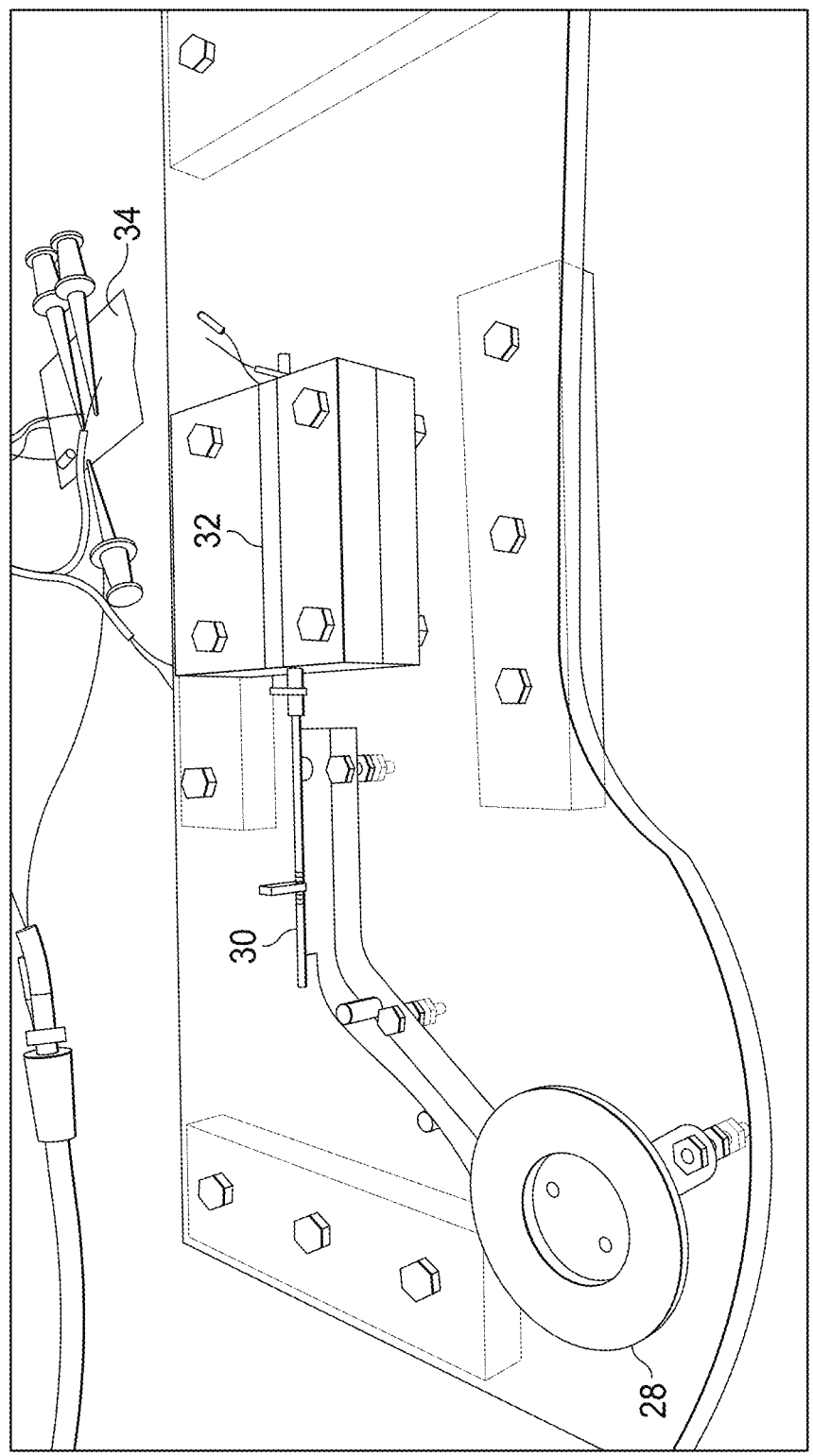
FIG. 9 illustrates one embodiment of a platform or stage of the present invention.

FIG. 9 illustrates one embodiment of a platform or stage of the present invention, comprising: hand dial crank 28, EM probe 30, capillary tube containing sample 32, hard wired multipurpose PC board 34. In one embodiment, the EM probe is held in place by a non-conductive platform made out of acrylic sheets held together by nylon screws and nuts. A hand dial crank is used to slide samples in and out of the EM probe The capillary tubes used to hold the samples were Kimble Chase 0.8 mm internal diameter, 1.1 mm outer diameter borosilicate glass tubes. The circuit board used to hard-wire the EM probe was a Multipurpose PC Board with 417 Holes (Model: 276-150).

Figure 10:
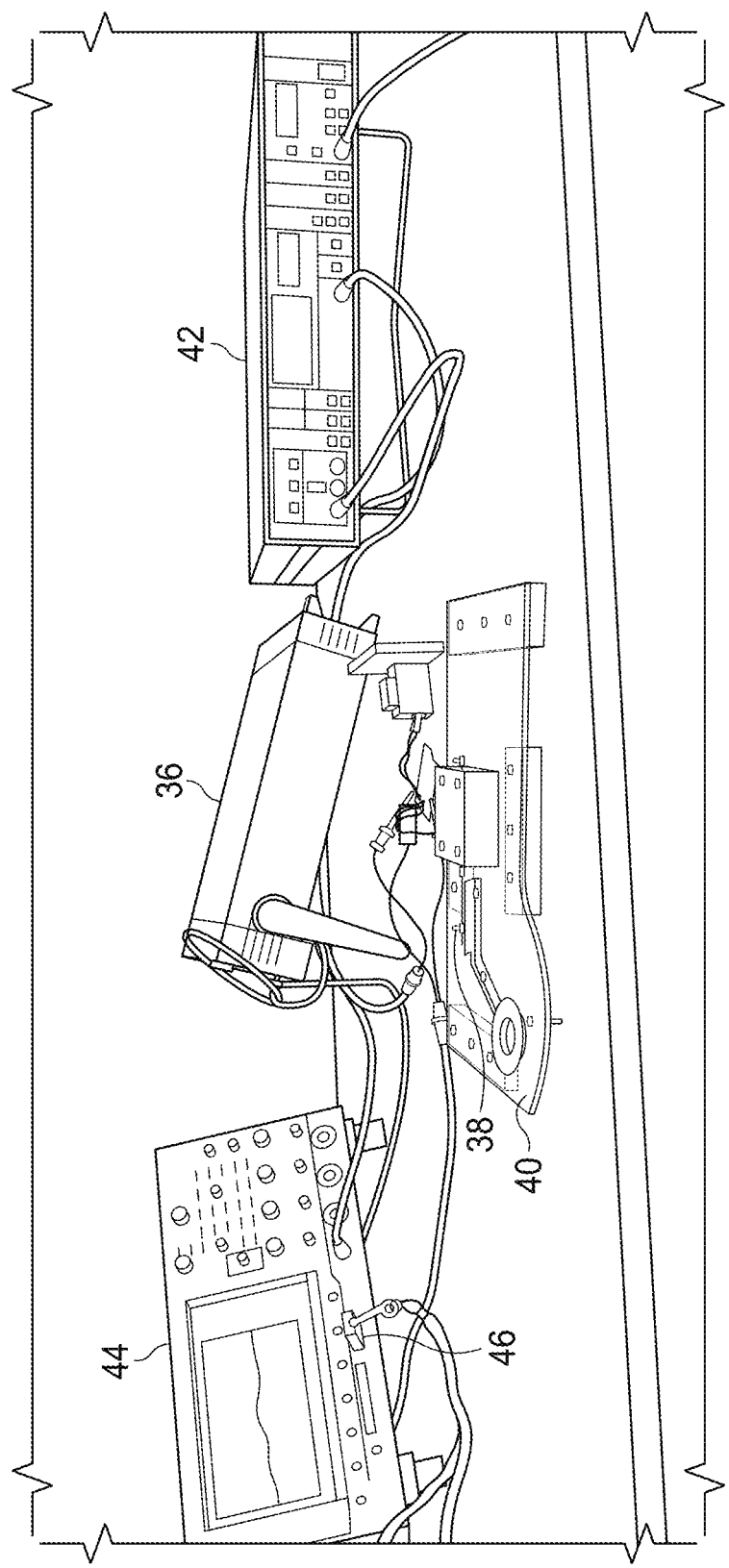
FIG. 10 illustrates one embodiment of the complete measurement set of the present invention.

FIG. 10 illustrates one embodiment of the complete measurement set of the present invention. Complete data collection and EM probe measurement set-up is preferably comprised of: function generator 36, EM probe 38, stage 40, lock-In amplifier 42, oscilloscope 44, flash drive 46 for data storage.

For measurement of particle mass, an Ohaus Analytical Plus AP250D balance was used. This scale has a 250 g weighing capacity and resolution of 0.1 mg. The iron particle samples were generated using Alfa Aesar iron powder, −325 mesh, reduced, 98% (metals basis).

The following discussion outlines the procedures used to detect small iron oxide particles with the eventual aim of detecting the food vacuoles of PF. This section will describe the procedure for optimizing the probe, preparation of iron oxide samples, and the procedure for conducting the EM detection measurements on the iron particle samples.

Procedure for Optimizing the EM Probe

Procedure for Selecting Most Sensitive Coil Arrangement

In earlier works on the detection of cancer, it was found that the sensitivity of a given probe could be increased by finding the optimum among four different arrangements of how the inner coil or the outer coil as the primary are connected to the external circuit. For the EM probe used for the present invention, eight different arrangements were analyzed. The reason for examining the four additional arrangements with the outer coil acting as the primary side of the probe is to determine if there was an advantage to using the inner coil as the detector since the sample would be placed inside.

Figure 11:
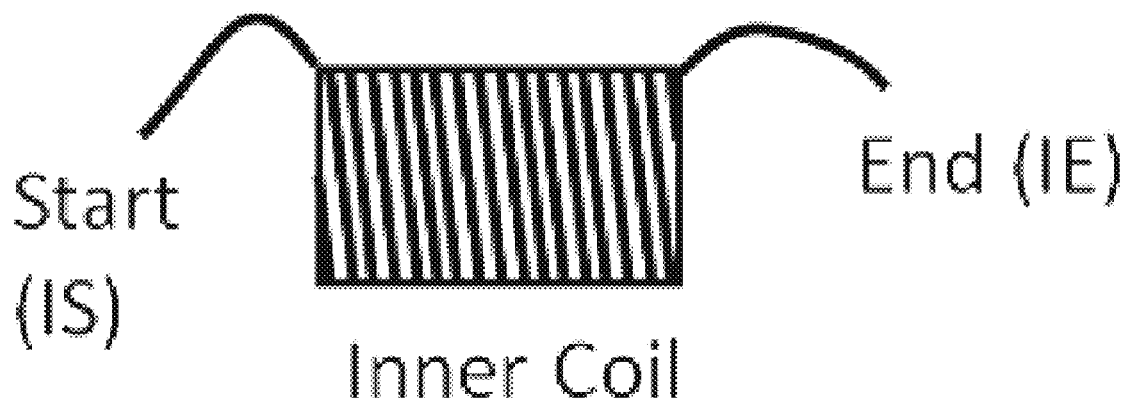
FIG. 11 illustrates one embodiment of the inner coil.
Figure 12:
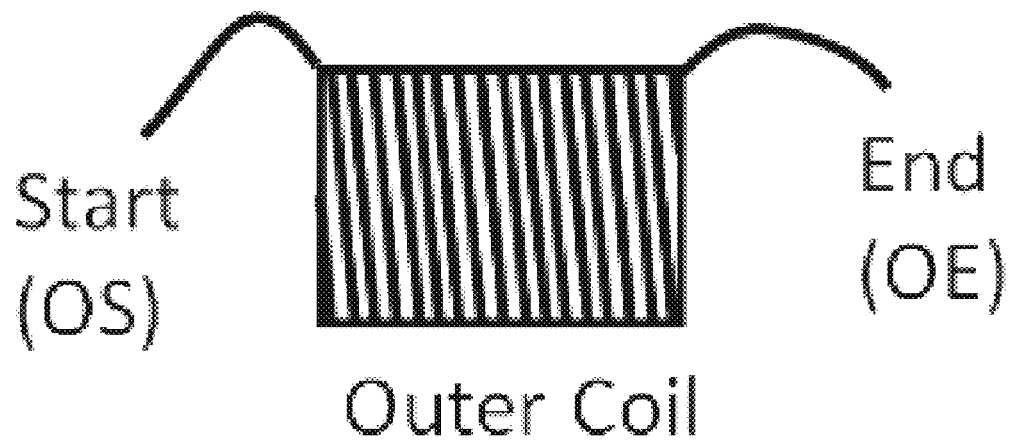
FIG. 12 illustrates one embodiment of the outer coil.

The coils are labeled according to the schemes shown in FIGS. 11 and 12. FIG. 11 illustrates one embodiment of the inner coil 48. FIG. 12 illustrates one embodiment of the outer coil 50. The beginning of the inner coil is labeled IS, with the inner coil end labeled IE. The outer coil follows the same nomenclature with the start of the outer coil labeled OS and the outer coil end labeled OE. In a 1 by 1 coil, either end could be labeled as the start or end but each wire was colored differently in order to distinguish them.

There are four arrangements explored with the inner coil connected to the function generator and switching the outer and inner coil leads. These arrangements are more easily understood as listed in Table 3, where the inner coil is the primary coil, and in Table 4 where the outer coil is the primary coil.

TABLE 3

Four coil arrangements when the inner coil driven by Function Generator

| φ | IS+ | IE− | IS− | IE+ |
|---|---|---|---|---|
| OS+ |  | IS-OS |  | IE-OS |
| OE− |  |  |  |  |
| OS− |  | IS-OE |  | IE-OE |
| OE+ |  |  |  |  |

TABLE 4

Four coil arrangements when the outer coil driven by Function Generator

| φ | IS+ | IE− | IS− | IE+ |
|---|---|---|---|---|
| OS+ |  | OS-IS |  | OS-IE |
| OE− |  |  |  |  |
| OS− |  | OE-IS |  | OE-IE |
| OE+ |  |  |  |  |

Measurements on the 659 μm solid iron particle were conducted using these eight unique arrangements to determine which arrangement yields the largest voltage difference and thus is most sensitive. The settings used for these measurements are listed in Table 5. The results from these measurements are discussed below in more detail.

TABLE 5

Instrument settings for coil arrangement experiments

| Instrument | Option | Setting |
| --- | --- | --- |
| Function Generator | Waveform | Sawtooth |
|  | Frequency | 99 kHz |
|  | Voltage | 7 Vpp |
| Lock-In Amplifier | Signal Input | A |
|  | Sensitivity | 2 mV |
|  | Dynamic Resolution | Norm |
|  | All Offsets | Off |
|  | All Expands | X1 |
|  | Display | R□ ϕ |
|  | Mode | F |
|  | Trigger | Sine |
|  | Time Constant Pre | 1 s |
|  | Time Constant Post | 0.1 s |
|  | Bandpass Filter | Out |
|  | Line Filter | Out |
|  | Line x2 Filter | Out |

Procedure for Selecting Optimum Ballast Resistance

The ballast resistance is an important part in the circuit system. The resistance that is connected between the function generator and the EM probe (FIG. 8) serves to keep the current in the circuit constant. If the ballast resistance is too high, current is reduced and the magnitude of the voltage differences between sample and null (no sample) decreases. If the ballast resistance is too low, sensitivity to a sample can be reduced as inductance begins to dominate. For these reasons, it is important to have a ballast resistance that is ideal for the EM probe to be able to detect small amounts of iron.

To determine which ballast resistance will be the best, arrays of different resistances are individually placed in the circuit and an oscilloscope trace is taken of the voltage variation over a single cycle of the optimum coil arrangement as found in the previous section. These oscilloscope outputs are analyzed to find the effect of the added resistance and if it is destroying peaks or causing too little of a voltage difference between peaks. The settings used for these measurements are listed in Table 6. The voltage was increased from 7 Vpp to 10 Vpp to allow for a larger voltage drop of the sawtooth wave resulting in higher dB/dt and increasing the induced voltage in the detector coil by Faraday. The results of these measurements are discussed in further detail below.

TABLE 6

Instrument settings for ballast resistance experiments

| Instrument | Option | Setting |
| --- | --- | --- |
| Function Generator | Waveform | Sawtooth |
|  | Frequency | 99 kHz |
|  | Voltage | 10 Vpp |

Procedure for Finding Optimum External Capacitance

In earlier works, it was discovered that the sensitivity of a given EM probe can be enhanced by adding a small amount of capacitance in the external circuit of the detector, regardless of any variability introduced during the fabrication process of the coil. In an effort to optimize PF1 and PF2 to be able to detect small iron islands such as the food vacuoles of PF, capacitance was added in a systematic manner to the external circuit of the detector coil. The procedure by which this was done is described here and the results are discussed in more detail below.

First, a variable capacitor ranging from 10 pF to 100 pF was hardwired into the multipurpose board. This variable capacitor was easily adjusted using a dial knob. Using the 659 μm particle as the sample, the variable capacitor was adjusted in 10 pF increments (starting from 10 pF) and measurements were recorded with and without the sample.

There were four variable external capacitance experiments conducted each with a different ballast resistance (1020 Ω, 800 Ω, 390Ω, and 2200Ω). This was an experiment to see how the variable external capacitance affected the sensitivity while also analyzing how the varying ballast resistance affected the sensitivity as well. The settings for the external capacitance experiments are given in Table 7.

TABLE 7

Instrument settings for coil arrangement experiments

| Instrument | Option | Setting |
| --- | --- | --- |
| Function Generator | Waveform | Sawtooth |
|  | Frequency | 99 kHz |
|  | Voltage | 10 Vpp |
| Lock-In Amplifier | Signal Input | A |
|  | Sensitivity | 2 mV |
|  | Dynamic Resolution | Norm |
|  | All Offsets | Off |
|  | All Expands | X1 |
|  | Display | R□ ϕ |
|  | Mode | F |
|  | Trigger | Sine |
|  | Time Constant Pre | 1 s |
|  | Time Constant Post | 0.1 s |
|  | Bandpass Filter | Out |
|  | Line Filter | Out |
|  | Line x2 Filter | Out |

Preparation of Iron Oxide Samples

Experiments for optimizing the EM probe were conducted on a 659 μm sized solid iron (oxide) particle. Additional measurements to explore the sensitivity of the EM probe to small particles were made on other samples of iron oxide particles generated using the procedure described herein.

First, the mass of all the capillary tubes used for samples were measured using the Ohaus scale. Each tube was stored separately and labeled. Iron oxide powder (Alfa Aesar, 325 mesh, less than 44 μm in size per particle) was used to produce samples of different amounts and agglomerated sizes within the capillary tubes. The powder was placed into a small glass container with deionized water and then shaken by a vortex mixer until thoroughly mixed. Allowing about a minute for the larger particles to settle to the bottom of the glass container, the 0.8 mm internal diameter capillary tubes were inserted at various depths inside the mixture to provide several different concentrations. Through capillary action samples of iron particles and deionized water were drawn into the tubes. These capillary tubes with the samples were then placed in a fume hood to allow for increased air flow and the water was allowed to evaporate. Once the samples were completely free of any water, their masses were measured again. The difference in mass between the tube with the sample and just the tube alone was recorded as the mass of the sample alone. Table 8 lists the mass, volume and estimated equivalent spherical diameter of the samples.

TABLE 8

Iron Particle Samples

| Sample | Mass (±0.2E-4 g) | Volume (μm³) | Estimated Equivalent Diameter** (μm) |
|---|---|---|---|
| Empty Tube | — | — | — |
| Particle | 11.(8)E-4 | 149.9E+06 | 659.0 |
| 1* | (0.04E-4) | 0.5E+06 | 95.8 |
| 2 | 0.(2)E-4 | 2.5E+06 | 169.3 |
| 3 | 0.(5)E-4 | 6.4E+06 | 229.8 |
| 4* | (0.04E-4) | 0.5E+06 | 98.7 |
| 5* | (0.05E-4) | 0.6E+06 | 104.8 |
| 6 | 0.(8)E-4 | 10.2E+06 | 268.7 |
| 7 | 5.(4)E-4 | 68.6E+06 | 507.8 |
| 8 | 1.(2)E-4 | 15.2E+06 | 307.6 |
| 9 | 1.(1)E-4 | 14.0E+06 | 298.8 |

*Volume estimated using microscope images
**Assumption: All particles combined equal perfect sphere The mass was found using the scale for all samples but 1, 4 and 5. With a mass, the volume could be found knowing that the density of the iron powder used is 7.874 ($10^{-12}$) g/μm³ [Alfa Aesar]. For samples 1, 4, and 5, the volume was estimated using the microscope images of the iron particles as the scale did not read any change in mass and then the mass was estimated using the density. The estimated equivalent diameter is an assumption that all of the particles are combined into one perfect sphere to make it easier to compare between the samples. The diameter was found using the volume and finding the diameter of a sphere:

$$V_{sphere} = \frac{4}{3}\pi r^3 => D = 2\left(\sqrt[3]{\frac{V_{sphere}}{\frac{4}{3}\pi}}\right)$$

PF1 Voltage Difference with 659 μm Iron Particle

Experiments using the prototype PF1 were conducted with the IS-OS coil arrangement in which the current was driven through the start of the inner coil with the signal detected through the outer coil by the lock-in amplifier (the start of the outer coil or OS is connected to the input of the lock-in amplifier while the end of the outer coil, OE is grounded). While this orientation gives the largest output signal, it is not necessarily optimal for having the largest difference in signal between sample and null.

Figure 13:
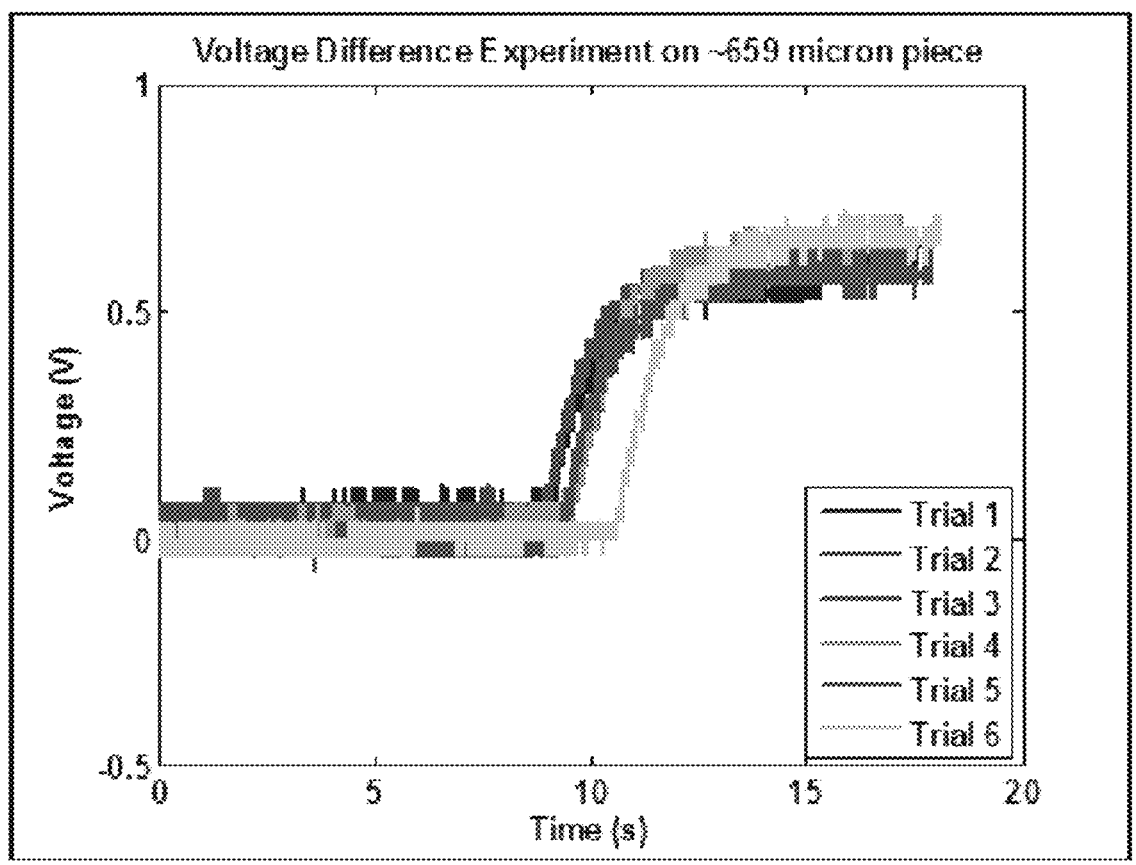
FIG. 13 illustrates oscilloscope output showing the voltage difference when a 659 μm iron particle is placed inside PF1.

In preliminary experiments, the solid 659 μm iron particle was used as the sample to determine whether the detectable signal was larger when the sample was placed outside of the probe (PF1) or when it was placed inside the probe. Six different trials were conducted to ensure that the measurement was repeatable. For each trial, the sample was completely outside of the coil and was slid inside using the stage described previously. This experiment was conducted with a 1020Ω ballast resistance and the instrument settings are listed in Table 9 with the results shown in FIG. 13. FIG. 13 illustrates oscilloscope output showing the voltage difference when a 659 μm iron particle is placed inside PF1

TABLE 9

Instrument settings for PF1 experiment on a 659 μm iron particle

| Instrument | Option | Setting |
|---|---|---|
| Function Generator | Waveform | Sawtooth |
| | Frequency | 99 kHz |
| | Voltage | 7 Vpp |

TABLE 9-continued

Instrument settings for PF1 experiment on a 659 μm iron particle

| Instrument | Option | Setting |
|---|---|---|
| Lock-In Amplifier | Signal Input | A |
| | Sensitivity | 2 mV |
| | Dynamic Resolution | Norm |
| | All Offsets | Off |
| | All Expands | X1 |
| | Display | R□ φ |
| | Mode | F |
| | Trigger | Sine |
| | Time Constant Pre | 1 s |
| | Time Constant Post | 0.1 s |
| | Bandpass Filter | Out |
| | Line Filter | Out |
| | Line x2 Filter | Out |
| | Reference | −48.4° |

As can be seen from FIG. 13, the average voltage difference between sample and null is 0.6041 volts with a standard deviation of 0.0418 volts. FIG. 13 shows that the results are very reproducible and the standard deviation helps to solidify this claim. This signal is quite substantial as the sensitivity setting on the lock-in amplifier can be reduced resulting in much higher sensitivity with the probe yet to be fully optimized. However, due to the inner diameter of PF1 being only 0.35 mm in diameter larger than the capillary tubes that were slid inside it, the insulation layer was beginning to be damaged and a second coil was made. The second prototype PF2 was therefore fabricated, optimized, and henceforth the results presented relate to PF2.

Prototype PF2

Figure 14:
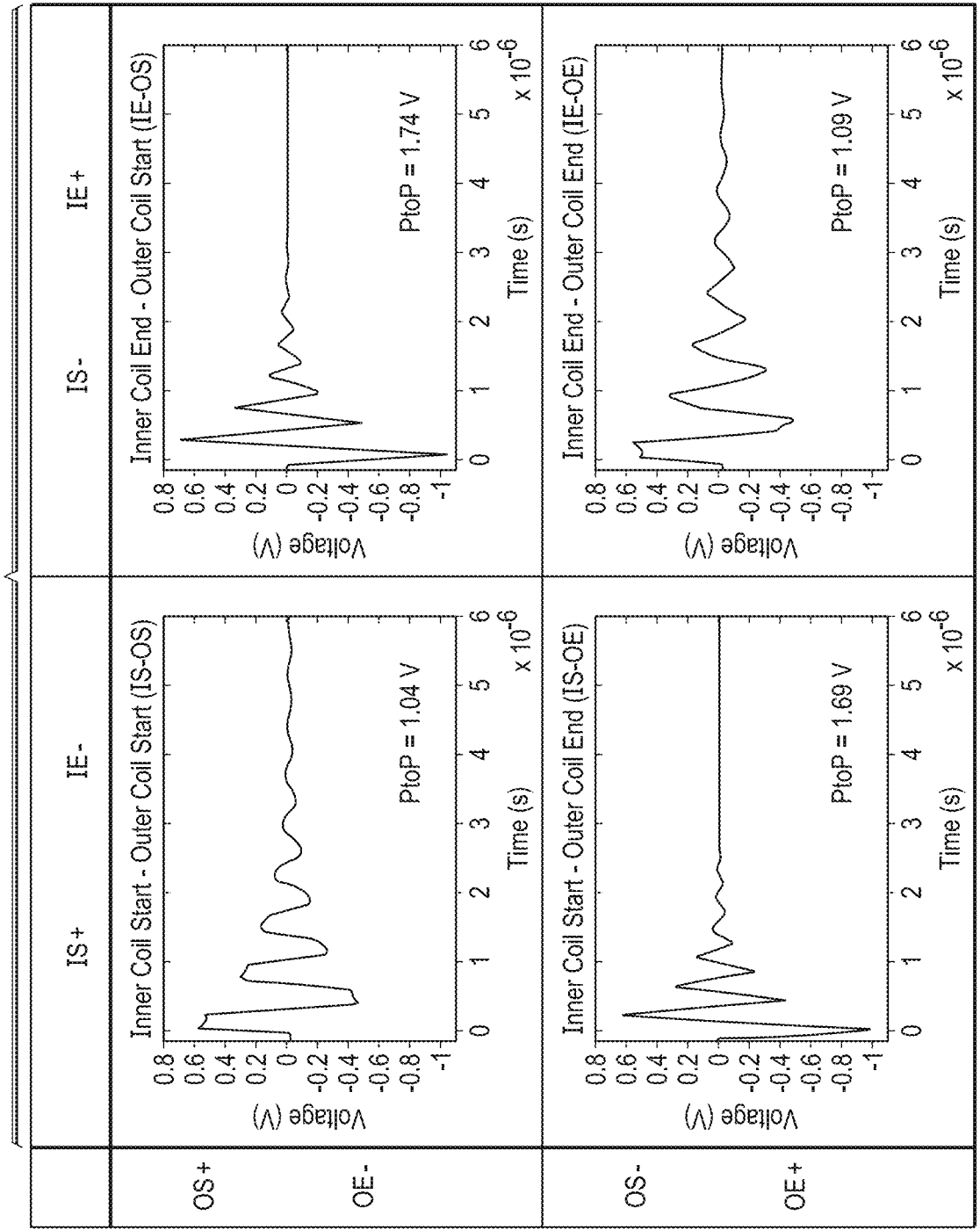
FIG. 14 illustrates PF2 oscilloscope traces for each coil arrangement with inner coil as the primary.
Figure 15:
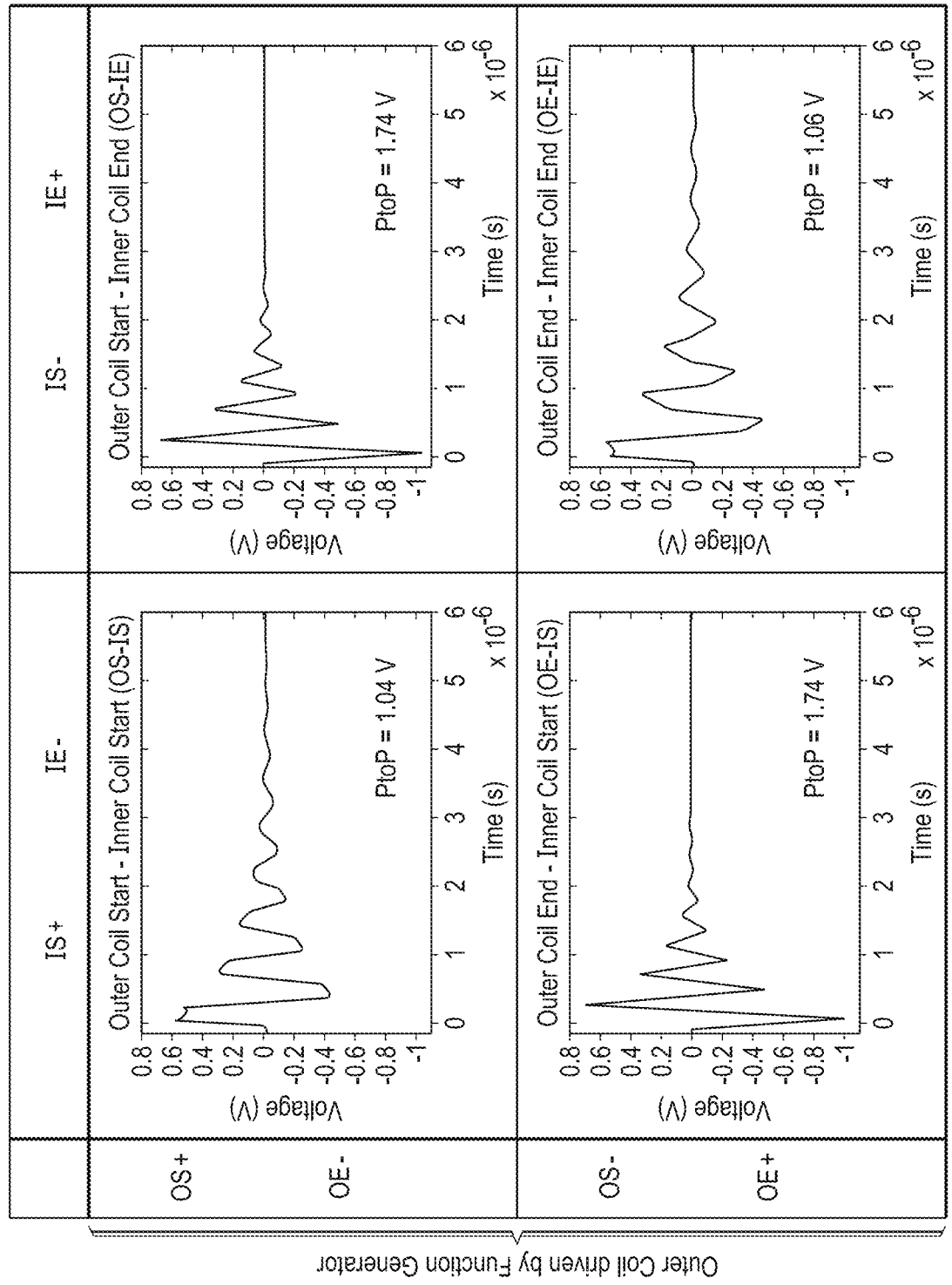
FIG. 15 illustrates PF2 oscilloscope traces for each coil arrangement with outer coil as the primary.

Eight unique orientations of PF2 were analyzed to determine which was the most sensitive and thus the best arrangement to use for measurements on the micron sized iron particles and food vacuoles. Oscilloscope traces were taken for each arrangement. The recorded voltage traces for each orientation for one period are shown in FIGS. 14 and 15. FIG. 14 illustrates PF2 oscilloscope traces for each coil arrangement with inner coil as the primary. FIG. 15 illustrates PF2 oscilloscope traces for each coil arrangement with outer coil as the primary.

From the results shown in FIGS. 14 and 15, it can be seen that the arrangements IE-OS, OS-IE, and OE-IS all result in the same Peak to Peak voltage (PtoP) as measured by the oscilloscope of ~1.74 V. Each of the eight arrangements were then used to measure the difference in signal between sample and null for the 659 μm particle. The results of these experiments for each arrangement are given in Tables 10 and 11.

TABLE 10

PF2 voltage differences (in mV), between sample present and null, with the inner coil as the primary

| φ | IS+ | IE− | IS− | IE+ |
|---|---|---|---|---|
| OS+ | IS-OS | | IE-OS | |
| OE− | 57.650 ± 2.631 | | 130.375 ± 3.221 | |
| | (Ref: +31.4°) | | (Ref: −165.7°) | |
| OS− | IS-OE | | IE-OE | |
| OE+ | 84.514 ± 2.093 | | 98.314 ± 5.943 | |
| | (Ref: −159.4°) | | (Ref: +27.5°) | |

TABLE 11

PF2 voltage differences (in mV), between sample present and null, with the outer coil as the primary

| φ | IS+ | IE− | IS− | IE+ |
|---|---|---|---|---|
| OS+ | OS-IS | | OS-IE | |
| OE− | 7.734 ± 4.379 | | 47.696 ± 5.894 | |
| | (Ref: +32.4°) | | (Ref: −157.2°) | |
| OS− | OE-IS | | OE-IE | |
| OE+ | 42.855 ± 7.933 | | 118.930 ± 5.158 | |
| | (Ref: −158.0°) | | (Ref: +30.3°) | |

Figure 16:
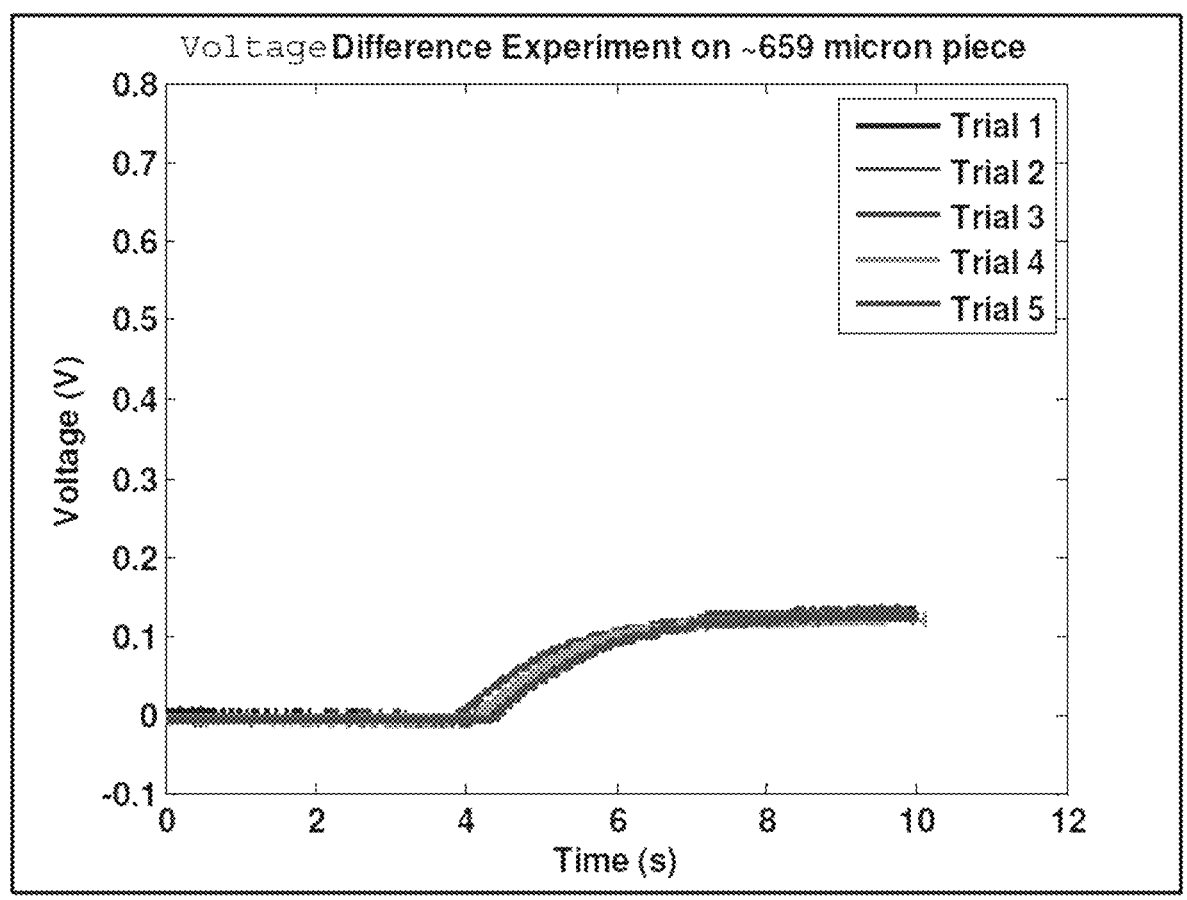
FIG. 16 illustrates oscilloscope output showing the voltage difference when a 659 μm iron particle is placed inside PF2 for the IE-OS arrangement.

Each arrangement is labeled, and average voltage difference (in mV) between sample and null along with the corresponding standard deviation is given. The reference phase (in degrees) as read on the lock-in amplifier is also included for uses in repeating this experiment. From these results, it is noticed that the IE-OS arrangement produces the greatest voltage difference and is therefore considered the most sensitive arrangement. The oscilloscope output as read from the lock-in amplifier for the IE-OS orientation is shown in FIG. 16. FIG. 16 illustrates oscilloscope output showing the voltage difference when a 659 μm iron particle is placed inside PF2 for the IE-OS arrangement.

The average voltage difference between sample and null (for the 659 μm particle) for the most sensitive arrangement of PF2, labeled as IE-OS, was measured to be 0.1304 V with a standard deviation of 0.0032 volts. Since all of the parameters for the function generator (input) and for the lock-in amplifier (output) were maintained the same as the preliminary measurements conducted with PF1 and given in Table 9, the performance of PF1 and PF2 can be directly compared. When comparing the average voltage difference it is noticed that PF1 (0.6041±0.0418 V) produces an average voltage difference over 4.5 times larger than the most sensitive arrangement of PF2 (0.1304±0.0032 V). This is most likely due to the smaller diameter of PF1. The EM probe inner coil for PF2 is 0.925 mm further away from the sample than that of PF1 which is about 0.325 mm away from the sample. This places the inner coil of PF2 over 3 times further away from the sample than PF1, likely resulting in the decrease in signal for PF2.

Optimum Ballast Resistance for PF2

The purpose of adding a ballast resistance is to enable the current on the primary side to follow the applied voltage as much as possible. There is a trade-off between the amount of current that is allowed through the primary coil with the greater that current, the greater the voltage difference between sample and null obtained on the detector coil. But if there is not enough resistance, the characteristics of the EM probe are distorted as inductance begins to take over leading to lower sensitivity. This is evident when six different ballast resistances were tested to determine which would be the optimal one to use. The resistors used were the original 1020Ω, along with five others; 200 Ω, 450 Ω, 630 Ω, 677Ω and 800Ω.

It was determined that anything below a ballast resistance of 800Ω resulted in distortion of the detector coil voltage and likely lower detectable signal. In addition, since the smallest resistor without destroying the signal is desired, the 800Ω resistor was selected over the 1020Ω resistor. Additional checks with ballast resistance were conducted at the same time as varying the external capacitance on the detector side. These results are discussed in further detail below.

Optimizing PF2 with Externally Added Capacitance

Figure 17:
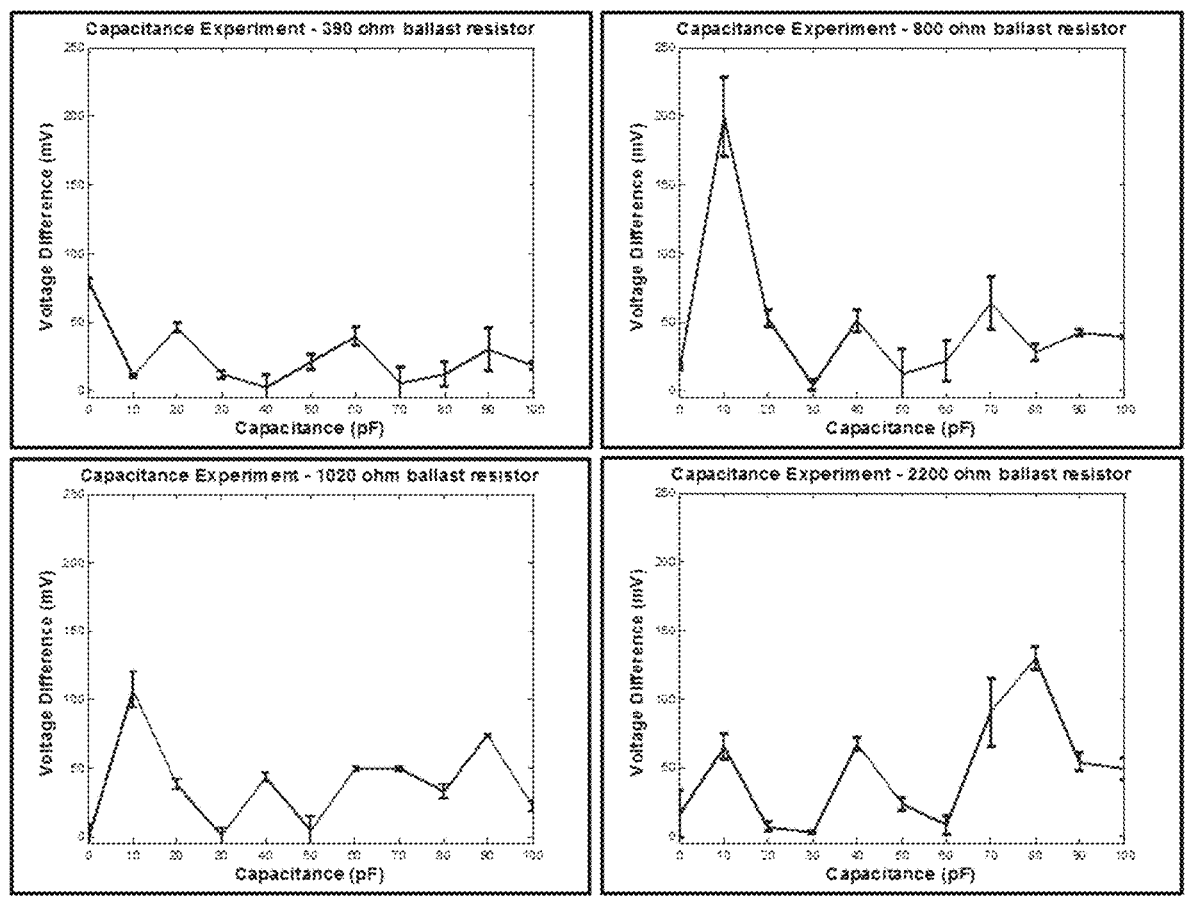
FIG. 17 illustrates the results of the PF2 capacitance experiment for four ballast resistors.

Four experiments varying external capacitance using unique ballast resistances (390 Ω, 800 Ω, 1020Ω, and 2200Ω) were conducted. These measurements were conducted on the 659 μm iron particle. The external capacitance was varied using a variable capacitor, which allowed measurements from 10 pF to 100 pF. A measurement was performed with 0 pF, with the variable capacitor removed. The results of each of these experiments is shown in FIG. 17. FIG. 17 illustrates the results of the PF2 capacitance experiment for four ballast resistors.

It was found that adding external capacitance on the detector side of the circuit does improve the sensitivity of the detection. Only the experiment with a 390Ω ballast resistance did not show improvement when adding external capacitance. Each of the 800 Ω, 1020Ω, and 2200Ω experiments have settings where the added external capacitance greatly increases the signal at a particular value of the external capacitance. The 390Ω resistor was tested to observe what would happen to the sensitivity when the ballast resistance was cut in half. When this did not produce better results than with the 800Ω resistor, the ballast resistance was doubled to that of the original ballast resistance of 1020Ω, at 2200Ω. This was also a check to determine which ballast resistance would be the optimal one following the previous experiment described. These results show that the initial selection of 800Ω for the ballast resistance was indeed the most optimal resistor of those tested.

Figure 18:
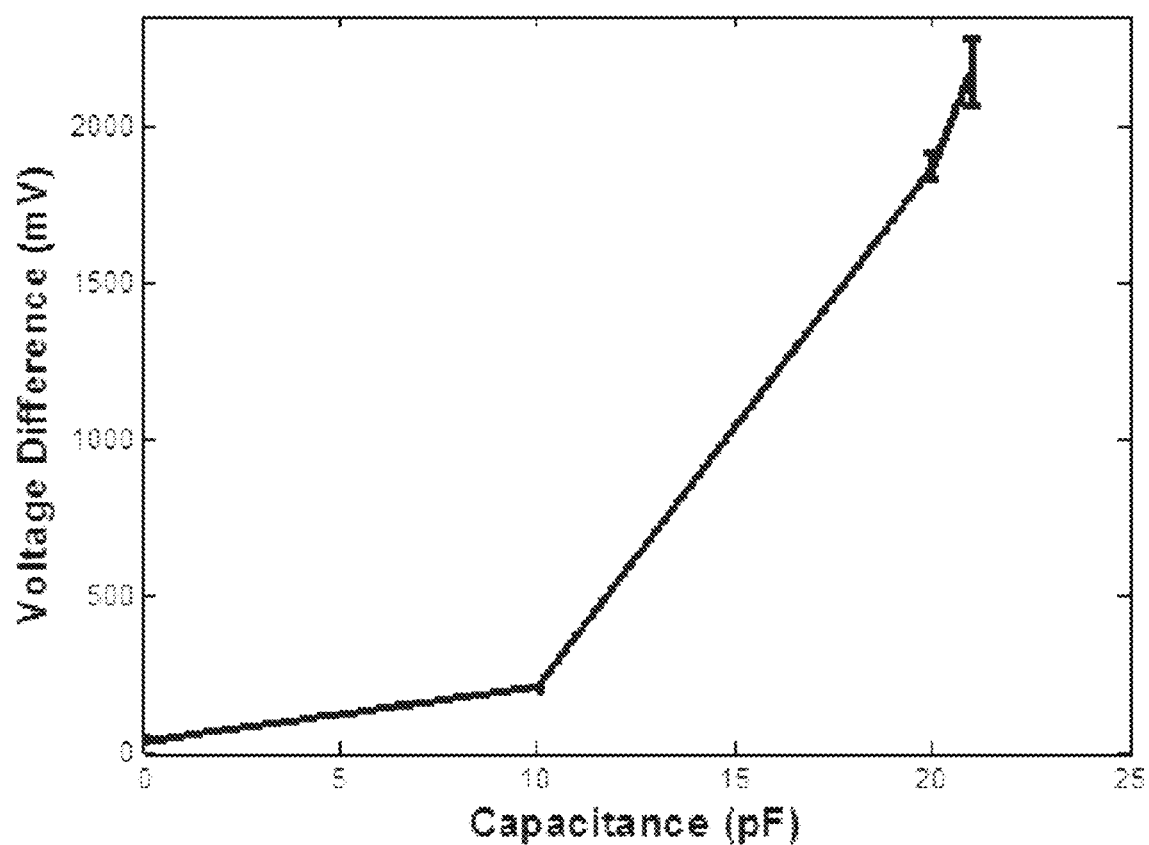
FIG. 18 illustrates results for a PF2 capacitance experiment for 800Ω resistor on Dynamic Reserve of Low.

All aforementioned optimizations were conducted with the lock-in amplifier's Dynamic Reserve setting at Normal. The configuration with an 800Ω ballast resistance was then examined with the lock-in amplifier dynamic reserve setting set to Low. The dynamic reserve adds a bandpass filter of 20 dB when the setting is changed from "Low" to "Normal". For a dynamic reserve of Low, the bandpass filter is 20 dB and for Normal it is 40 dB. At a Low setting, it is expected for the sensitivity to increase as the filter is not as sharp, but this will also result in an increase in the noise. In addition, at this Low setting, only so much capacitance can be added to the detector external circuit without overloading the Lock-in amplifier. For the case with the 800Ω ballast resistor, the optimum external capacitance was found to be about 25 pF without overloading the lock-in amplifier. The results of optimizing for external capacitance are shown in FIG. 18. FIG. 18 illustrates results for a PF2 capacitance experiment for 800Ω resistor on Dynamic Reserve of Low.

In summary, the measurements on the 659 μm particle show great increase in sensitivity with about 20 pF of external capacitance added to the detector coil circuit when the Dynamic Reserve is set to Low. This increase results in a signal that is 10 times larger than that of any voltage difference observed with the Dynamic Reserve offset at Normal. Due to this substantial increase in signal difference between sample and null, this configuration was chosen for measurements on the food vacuoles isolated from PF and trapped in a capillary tube.

Preliminary Measurements on PF Food Vacuoles Using Prototype PF2

Food vacuoles isolated from PF infected human blood were trapped inside a thin capillary tube by applying a strong magnetic field of ~35 T in less than 10 pulses lasting a few microseconds.

These food vacuoles were estimated to have a volume of about 15710 μm$^3$ for agglomeration 1 and 47120 μm$^3$ for agglomeration 2. This results in a total volume of about 62830 μm$^3$ in the test section within the EM probe and if this is considered to be one spherical mass, the estimated equivalent diameter of all the food vacuoles combined would be about 50 µm. With the sample thus identified and sized, the settings used for detection experiments with the EM probe are given in Table 12.

TABLE 12

Instrument settings for PF2 experiment on ~50 µm food vacuoles

| Instrument | Option | Setting |
|---|---|---|
| Function Generator | Waveform | Sawtooth |
| | Frequency | 99 kHz |
| | Voltage | 10 Vpp |
| Lock-In Amplifier | Signal Input | A |
| | Sensitivity | 2 mV |
| | Dynamic Resolution | Low |
| | All Offsets | Off |
| | All Expands | X1 |
| | Display | R□ φ |
| | Mode | F |
| | Trigger | Sine |
| | Time Constant Pre | 3 s |
| | Time Constant Post | 0.1 s |
| | Bandpass Filter | Out |
| | Line Filter | Out |
| | Line x2 Filter | Out |

These settings are nearly identical to those given previously where the EM probe was found to be most sensitive with an added external capacitance of a little over 20 pF on a Dynamic Reserve setting of "Low" on the lock-in amplifier. Only the pre-time constant is changed from 1 second to 3 seconds. This is done to reduce the noise so that when the signal is zoomed in on the oscilloscope, the fluctuations are reduced. Measurements are conducted on an empty glass capillary tube as control as well as on food vacuoles, and these results are shown in tabulated form in Table 13.

TABLE 13

Initial Food Vacuole testing

| Capacitance at ~21 pF | Voltage Difference (mV) |
|---|---|
| Empty glass tube | 16.2 ± 4.3 |
| Food Vacuoles (~50 µm) | 44.7 ± 25.7 |

The results presented in Table 13 show that there is evidence that the food vacuoles can be detected. However, under the conditions of these measurements, there was substantial noise and the entire circuit including the EM probe appeared to be sensitive to movement as far away as a foot away from the apparatus. Nevertheless, the data in Table 13 shows that there was signal when comparing measurements on the empty capillary tube and the capillary tube with the food vacuoles. Both the signal and the standard deviation are higher for the food vacuoles. This could be a result of the sample not positioned in the same location inside the probe for each trial. If the sample is at a different location within the probe, this will result in a seemingly random variation of the detected signal with each trial. While encouraging, these results can be repeated, for example with a different coil design that is more sensitive than PF2. Moreover, these encouraging results can be verified by repeating these measurements with food vacuoles suspended in solution, as they would not be agglomerated in vivo as long as the parasite remains within the red blood cells.

Measurements on Iron Oxide Particles Using PF2

Below, measurements on iron oxide particles of different effective sizes are presented. The samples are prepared according to the procedure described previously. Table 14 provides the measured signals as the amount of iron oxide particles is varied. Based on this data, the sensitivity curves shown in FIGS. 19-20 were constructed.

TABLE 14

Ordered results of iron particle testing using PF2

| Sample | Mass (±0.2E-4 g) | Volume (µm³)* | Estimated Equivalent Diameter** (µm) | Voltage Difference (mV) *** |
|---|---|---|---|---|
| Particle | 11.(8)E-4 | 149.9E+06 | 659.0 | 545.473 ± 13.170 |
| 7 | 5.(4)E-4 | 68.6E+06 | 507.8 | 363.844 ± 7.965 |
| 8 | 1.(2)E-4 | 15.2E+06 | 307.6 | 133.282 ± 17.706 |
| 9 | 1.(1)E-4 | 14.0E+06 | 298.8 | 119.544 ± 5.754 |
| 6 | 0.(8)E-4 | 10.2E+06 | 268.7 | 41.393 ± 3.824 |
| 3 | 0.(5)E-4 | 6.4E+06 | 229.8 | 14.901 ± 2.444 |
| 2 | 0.(2)E-4 | 2.5E+06 | 169.3 | 6.571 ± 2.752 |
| 5* | (0.05E-4) | 0.6E+06 | 104.8 | 4.711 ± 1.085 |
| 1* | (0.04E-4) | 0.5E+06 | 95.8 | 4.694 ± 2.408 |
| 4* | (0.04E-4) | 0.5E+06 | 98.7 | 2.521 ± 1.362 |
| Empty Tube | — | — | — | 1.718 ± 0.849 |

*Volume estimated using microscope images
**Assumption: All particles combined equal perfect sphere
*** Measurements obtained from importing oscilloscope data into MatLab allowing for measurements to 3 decimal places (i.e. microvolts)

Figure 19:
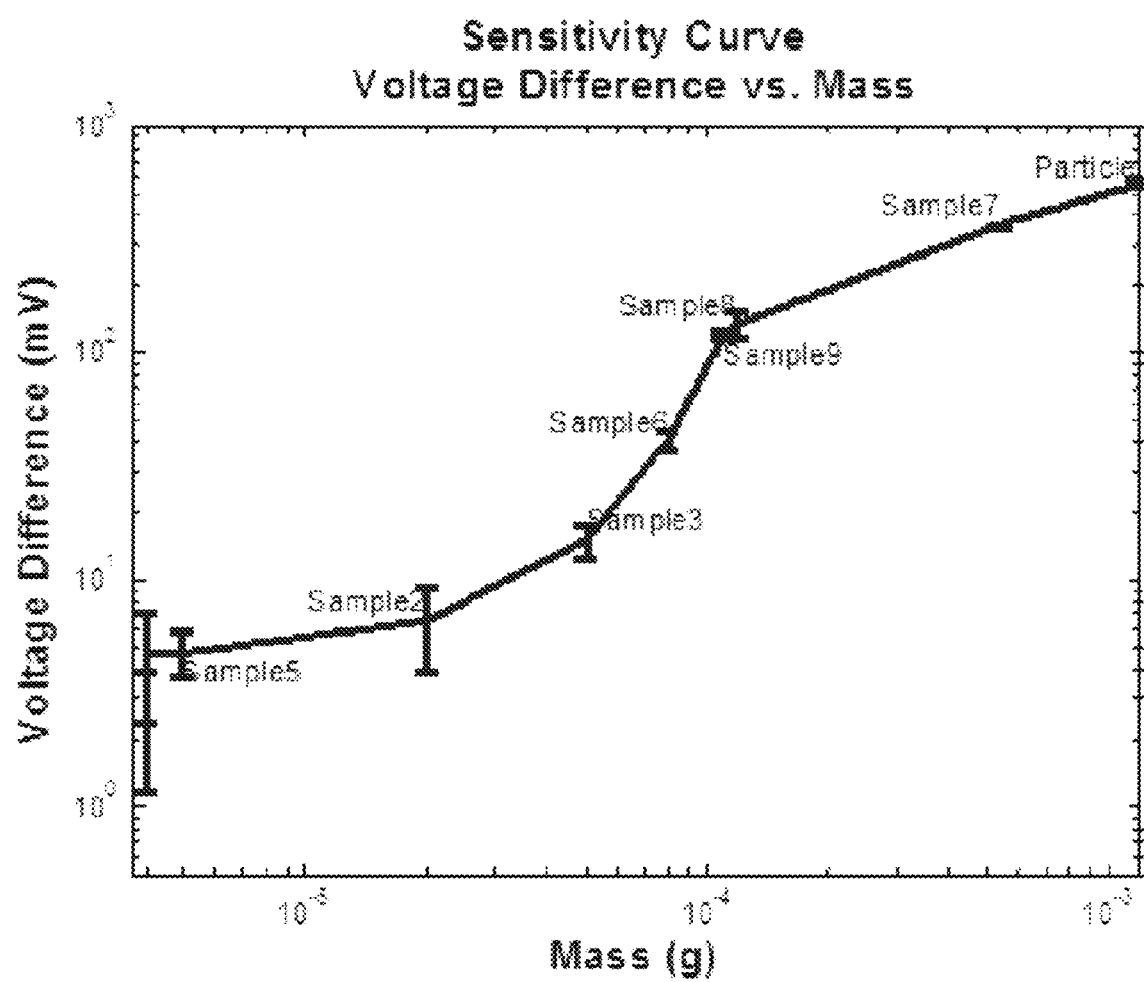
FIG. 19 illustrates a sensitivity curve for iron particle voltage difference versus mass with EM probe PF2.
Figure 20:
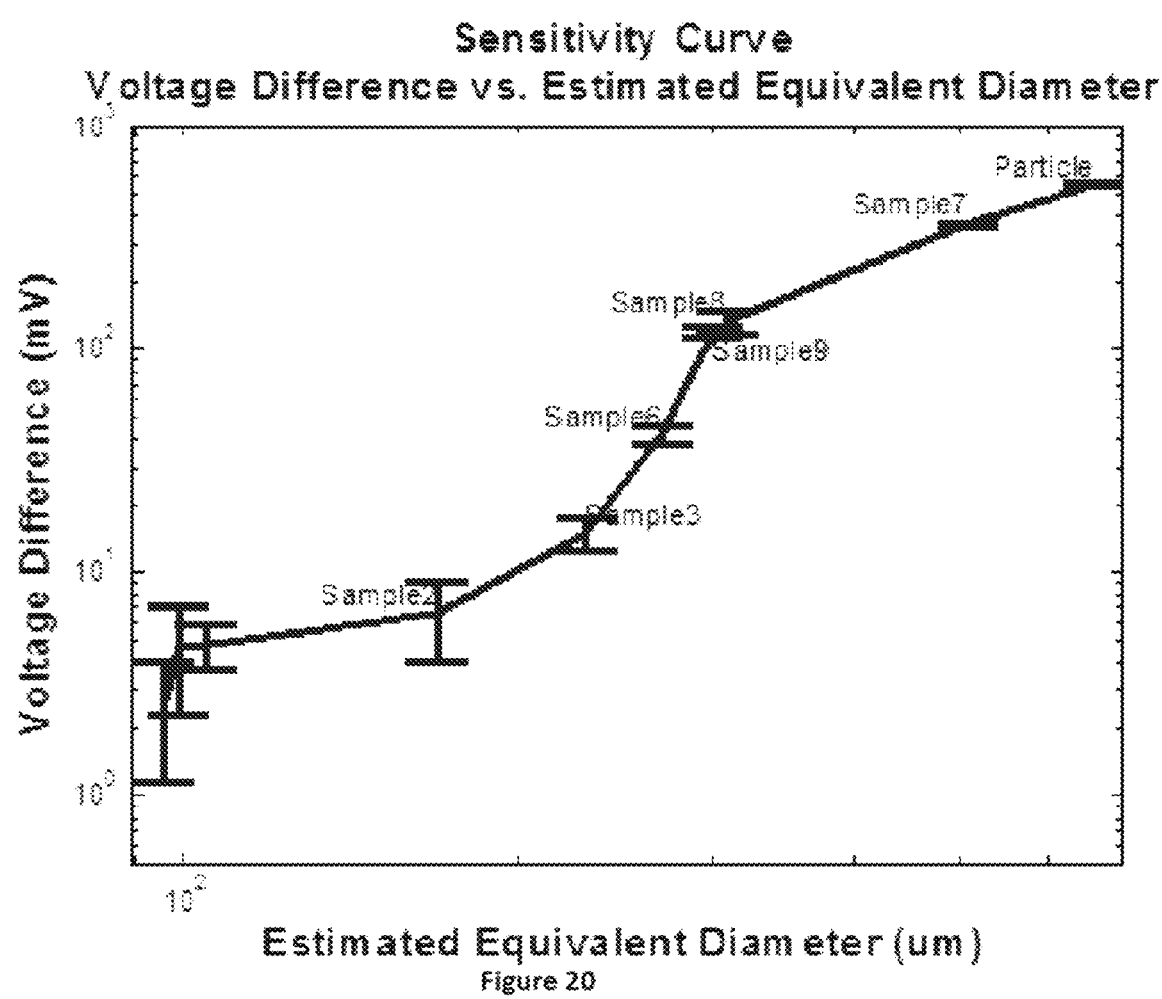
FIG. 20 illustrates a sensitivity curve for iron particle voltage difference versus estimated equivalent diameter with EM probe PF2.

The results presented in Table 14 and FIGS. 19-20 show as expected that the signal drastically decreases as the mass (and equivalent particle diameter) decrease. Not all samples had evenly distributed particles. In some samples, the particles were much more spread out than in others. Sample 7 in particular, is a sample that is spread throughout a capillary tube, and the resulting signal is well over half the signal obtained from the solid 659 µm particle even though the volume of Sample 7 is not quite half that of the solid 659 µm particle. This suggests that a more spread out distribution might yield a larger signal, and may in fact mimic the flow of infected erythrocytes in vivo. This result also suggests that performing measurements on food vacuoles in solution may be more relevant for the field application rather than the measurements on agglomerated iron oxide particles.

The results presented in this section show that particles on the scale of microns can be detected and the non-invasive approach of detecting malaria parasites of the present invention is feasible. Moreover, the sensitivity curves imply that if sufficient control is attained over signal to noise, then iron-rich particles much smaller than the ones considered here can be detected. However, while the sensitivity of the probe can be increased by reducing the sensitivity setting on the lock-in amplifier from 2 mV/V down to 20 mV/V, the noise may just be too large to collect any signal.

An EM probe for detecting iron-rich particles on the scale of microns and remnant food vacuoles from PF infected blood has been provided by the present invention. Measurements on different sized iron oxide particles demonstrate that detecting iron-rich islands on the scale of microns can indeed be detected. Measurements on actual food vacuoles isolated from human blood are encouraging and indicate despite the high noise level in the signal, may be feasible in vivo.

An important parameter that has been identified is the distance between the iron-rich target and the sensing surface of the EM probe. When comparing initial measurements with PF1 with those with PF2, the further the probe is away from the sample, the lower the detected signal and thus the lower the sensitivity of the probe. This is important to remember when designing the next generation EM probe in which the sample will be placed inside the coil, simulating a finger inserted into an EM probe.

The present invention also establishes that the probe can be optimized through changing external capacitance and modifying the ballast resistance in the circuit. By continuing to optimize these and other parameters, greater sensitivity can be attained with an accompanying reduction in noise.

The process applied in the processes described herein can be applied to detecting malaria parasites in vivo. A 5% level of parasitemia (i.e. 5% of red blood cells (RBC) infected with PF) results in a patient exhibiting symptoms. Since the typical concentration of RBCs in human blood is at least $4 \times 10^9$ cells/mL, and assuming a capillary of 1 mm length, and 10 μm diameter, the number of cells accessible over a 2 second period would be 314 cells per capillary. At a level of 5% parasitemia, that amounts to about 16 infected RBCs per capillary. The average density of capillaries in the middle finger has been measured and can be taken to be on the order of about 75 per mm². Therefore, in a field of about 1 cm², there would be 7500 capillaries and $\sim 1.2 \times 10^5$ infected RBCs. Assuming that each infected RBC contains 1 food vacuole, that is a minimum of $1.2 \times 10^5$ food vacuoles (taken to be 1 μm in size, an equivalent diameter of $1.2 \times 10^5$ μm) that must be detected. This is equivalent to an iron-rich hemozoin volume of $6 \times 10^{-8}$ cm³ ($6 \times 10^4$ (μm)³). Taking the density of hemozoin to be 1.49 g/cm³ [18], that amounts to an equivalent mass of $\sim 9 \times 10^{-8}$ g or about 100 ng over the 1 cm² detection area. This is about an order of magnitude (40 times) smaller than the smallest iron oxide particle as can be seen from the data in Table 14. However, 100 ng is exactly what was detected (albeit with a large standard deviation) as can be seen from Table 13 (50 μm effective diameter corresponds to $6.5 \times 10^{-8}$ cm³ or an effective hemozoin mass of $\sim 10^{-7}$ g or 100 ng). Therefore, the measurement of PF in vivo is feasible using the principles of the present invention. It is appreciated that there is considerable potential for attaining greater sensitivity by optimizing the EM probe with greater sensitivity.

While certain embodiments of the present invention are described in detail above, the scope of the invention is not to be considered limited by such disclosure, and modifications are possible without departing from the spirit of the invention as evidenced by the following claims:

What is claimed is:

1. A system for connecting to an alternating current or power supply for detecting the presence of malaria parasites in blood, comprising:
    a probe, in electrical communication with the current or power supply, shaped in a configuration so that it may be hand-held comprising a primary wire and a detector wire, the probe comprising a concentrically wound inner coil configured as the primary wire and outer coil configured as the detector wire, and wherein the inner coil is adapted to produce a magnetic field when a time varying voltage or current is applied to the inner coil, wherein the magnetic field induces a voltage or current in the outer coil through inductive coupling;
    a ballast resistor in electrical communication with the inner coil to enable a current on the inner coil to follow the applied time varying voltage or current and to maintain the current on the inner coil substantially constant;
    a capacitor in electrical communication with the outer coil;
    wherein the ballast resistor and capacitor have predetermined values selected to increase sensitivity of the probe and to reduce noise;
    wherein the probe is configured to sense a change in a signal on the detector wire when an iron particle is placed adjacent to the probe;
    a measurement system, operably connected to the probe and configured to measure a detectable difference in both phase shift and amplitude change in a voltage or current produced thereby in the detector wire when the primary and detector wires are positioned adjacent to the blood and when there is a presence of iron particles in the blood, the measurement system comprising:
        a lock-in amplifier in electrical communication with the probe for extracting the signal on the detector wire; and
    wherein sensitivity of the probe is increased by configuring the probe so that the primary wire serves as the inner coil, and the detector wire serves as the outer coil.

2. The system according to claim 1, wherein the probe is a coaxially wound dual coil wherein the dual coil is placed around a rod of spring steel.

3. The system according to claim 2, wherein the probe is configured so that a self-inductance of the inner coil is less than 69.6 μH and a self-inductance of the outer coil is less than 475.5 μH.

4. The system according to claim 1, wherein the self-inductance of the inner coil is about 2.4 μH and the self-inductance for the outer coil is about 4.5 μH.

5. The system according to claim 1, wherein the system is adapted to detect malaria by detecting the presence of magnetic particles in the blood.

6. The system according to claim 5, where the magnetic particles are iron rich particles called hemozoin.

7. The system according to claim 1, wherein the probe and measurement system are configured to detect detectable differences in both phase shift and amplitude change in the voltage or current produced thereby in the detector wire in the presence of iron particles on a scale of less than 44 microns.

8. The system according to claim 7, wherein the capacitor comprises capacitance between 10 pF and 100 pF and the ballast resistor comprises a ballast resistance between 390 ohms and 2200 ohms.

9. The system according to claim 1, wherein a diameter of the probe has a predetermined diameter selected to increase sensitivity of the probe.

10. The system according to claim 1, wherein a diameter of the probe is approximately 1.45 mm.

11. The system according to claim 1, wherein a diameter of the probe is between 1.25 mm and 1.66 mm.

12. The system according to claim 1, wherein the probe is comprised of one primary coil and one detector coil.

13. The system according to claim 1, wherein the ballast resistor comprises a ballast resistance of about 800 ohms and the capacitor comprises a capacitance of about 20 picofarads and wherein a dynamic reserve setting of the lock-in amplifier is set to low.

14. The system according to claim 1, wherein the malaria parasites comprise *Plasmodium falciparum*.

15. The system according to claim 1, wherein both the inner coil and the outer coil are concentrically wound.

16. The system according to claim 1, wherein the voltage or current produced in the detector wire has at least a first and second duty cycle each comprised of multiple peaks and wherein the primary wire and detector wire has inductances and capacitances so a last peak of the voltage or current produced in the first duty cycle coincides on a sloping side of a first peak of the second duty cycle.

17. The system according to claim 1, wherein a self-inductance of the inner coil is less than approximately 11.7 µH and a self-inductance of the outer coil is less than approximately 15.1 µH.

18. The system according to claim 1, wherein the alternating current or power supply is configured to provide a non-sinusoidal, asymmetric signal to the probe.

19. The system according to claim 1, wherein the lock-in amplifier configured to provide a DC output voltage indicative of a detected phase shift between the voltage or current on the primary wire and the voltage or current produced thereby in the detector wire.

20. The system according to claim 1 wherein the primary wire and detector wire are each comprised of a plurality of layers.

21. A system according to claim 1, further comprising an alert signal generated by the system when iron particles are detected by the system.

22. A system according to claim 1, wherein the iron particles are hemozoin.

23. The system of claim 1, wherein the lock-in amplifier extracts the signal on the detector wire from noise on the detector wire.

24. A system for connecting to an alternating current or power supply for detecting the presence of malaria parasites in blood, comprising:
   a probe, in electrical communication with the current or power supply, shaped in a configuration so that it may be hand-held comprising a primary wire and a detector wire, the probe comprising a coaxially wound inner coil configured as the primary wire and outer coil configured as the detector wire, and wherein the inner coil is adapted to produce a magnetic field when a time varying voltage or current is applied to the inner coil, wherein the magnetic field induces a voltage or current in the outer coil through inductive coupling;
   a ballast resistor in electrical communication with the inner coil to enable a current on the inner coil to follow the applied time varying voltage or current and to maintain the current on the inner coil substantially constant;
   a capacitor in electrical communication with the outer coil;
   wherein the ballast resistor and capacitor have predetermined values selected to increase sensitivity of the probe and to reduce noise;
   wherein the probe is configured to sense a change in a signal in the detector wire when an iron particle is placed adjacent to the probe;
   a measurement system, operably connected to the probe and configured to measure a detectable difference in both phase shift and amplitude change in a voltage or current produced thereby in the detector wire when the primary and detector wires are positioned adjacent to the blood and when there is a presence of iron particles in the blood, the measurement system comprising:
      a lock-in amplifier in electrical communication with the probe for extracting the signal on the detector wire;
   wherein sensitivity of the probe is increased by configuring the probe so that the primary wire serves as the inner coil, and the detector wire serves as the outer coil;
   wherein a capacitance of the capacitor is between 10 pF and 100 pF and a ballast resistance of the ballast resistor is between 390 ohms and 2200 ohms;
   wherein a diameter of the probe has a predetermined diameter selected to increase sensitivity of the probe;
   wherein the probe and measurement system are configured to detect detectable differences in both phase shift and amplitude change in the voltage or current produced thereby in the detector wire in the presence of iron particles on a scale of less than 44 microns.

25. The system of claim 24, wherein the probe is configured so that a self-inductance of the inner coil is less than 69.6 µH and a self-inductance of the outer coil is less than 475.5 µH.

* * * * *